(12) United States Patent  
Lai

(10) Patent No.: US 7,820,386 B2  
(45) Date of Patent: Oct. 26, 2010

(54) CANCER SCREENING METHOD

(75) Inventor: Hung-Cheng Lai, Taipei (TW)

(73) Assignee: National Defense Medical Center, Taipei (TW)

( * ) Notice: Subject to any disclaimer, the term of this patent is extended or adjusted under 35 U.S.C. 154(b) by 484 days.

(21) Appl. No.: 11/764,051

(22) Filed: Jun. 15, 2007

(65) Prior Publication Data

US 2008/0311570 A1    Dec. 18, 2008

(51) Int. Cl.
C12Q 1/68     (2006.01)
C12P 19/34    (2006.01)

(52) U.S. Cl. .............................. 435/6; 435/63; 435/64
(58) Field of Classification Search ....................... None
See application file for complete search history.

(56) References Cited

OTHER PUBLICATIONS

Cottrell (Clin. Biochem. 37(2004) 595-604).*
Verma et al. (Critical Review in Oncology/Hematology 60 (2006), pp. 9-18).*
N.B. Atkin et al.; DNA ploidy of cervical intraepithelial neoplasia (CIN); Journal; 1997; pp. 151-152; Cancer Genet Cytogenet; Elsevier Science Inc.,; New York.
Stephen B. Baylin et al.,; DNA hypermethylation in tumorigenesis: epigenetics joins genetics; Journal; Apr. 2000; pp. 168-174; vol. 16, No. 4; Trends in Genetics.
S.B. Baylin et al.,; "Alterations in DNA methylation: a fundamental aspect of neoplasia."; Journal; 1998; pp. 141-196; Adv Cancer Res.
AP Bird; CpG-rich islands and the function of DNA methylation; Journal; 1986; pp. 209-213; 321(6067); Nature.
Cheah, M. S., C. D. Wallace, et al.; "Hypomethylation of DNA in human cancer cells: a site-specific change in the c-myc oncogene."; Journal; 1984; pp. 1057-1065; J Natl Cancer Inst.
Gerda Egger et al.,; "Epigenetics in human disease and prospects for epigenetic therapy."; Journal; May 27, 2004; pp. 457-463; vol. 429; Insight Review Articles; Nature.
Andrew P. Feinberg et al.,; The history of cancer epigenetics.; Journal; Feb. 2004; pp. 143-153; vol. 4; Nature Review Cancer; Nature.
A.P. Feinberg et al.,; "Hypomethylation distinguishes genes of some human cancers from their normal counterparts."; Journal; 1983; pp. 89-92; Nature.
Qinghua Feng et al.,; Detection of hypermethylated genes in women with and without cervical neoplasia; Journal; Feb. 16, 2205; pp. 273-282; vol. 97, No. 4; Journal of National Cancer Institute.
Theresa M. Geiman et al.,; "Chromatin remodeling, histone modifications, and DNA methylation . . . "; Jounral; 2002; pp. 117-125; Journal of Cellular Biochemisty; Wiley-Liss, Inc.
P.E. Gravitt et al.,; Genotyping of 27 human papillomavirus types by using L1 consensus PCR products by a single-hybridization . . . ; Journal; Oct. 1998; pp. 3020-3027; vol. 36, No. 10; Journal of Clinical Microbiology; American Society for Microbiology.
Charles P. Harris et al.,; "Comprehensive molecular cytogenetic characterization of cervical cancer cell lines."; Journal; 2003; pp. 233-241; Genes Chromosomes Cancer; Wiley-Liss, Inc.

Olga L. Henao et al.,; "Women with polymorphisms of methylenetetrahydrofolate reductase (MTHFR) . . . "; Journal; 2004; pp. 991-997; Int J Cancer; Wiley-Liss, Inc.
Peter A. Jones et al.,; "Cancer epigenetics comes of age."; Journal; Feb. 1999; pp. 163-167; vol. 21; Nature Genetics; Nature America Inc.
Peter A. Jones et al.,; "The fundamental role of epigenetic events in cancer."; Journal; Jun. 2002; pp. 415-428; vol. 3; Nature Review Genetics.
A.M. Kersemaekers et al.,; "Loss of heterozygosity for defined regions on chromosomes 3, 11 and 17 in carcinomas of the uterine cervix."; Jounral 1998; pp. 192-200; Br J Cancer.
Alfred G. Knudson; "Two genetic hits (more or less) to cancer."; Journal; 2001; pp. 157-162; Vo. 1; Nat Rev Cancer; Macmillan Magazines Ltd.
A.G. Knudson et al.,;"Mutation and childhood cancer: a probabilistic model for the incidence of retinoblastoma."; Journal; 1975; pp. 5116-5120; vol. 7s; Proc Nati Acad Sci U S A.
Hung-Cheng Lai et al.,; Genetic polymorphism of the interferon-gamma gene in cervical carcinogenesis.; Journal; 2005; pp. 712-718; Int J Cancer; Wiley-Liss, Inc.
Peter W. Laird; The power and the promise of DNA methylation markers; Journal; Apr. 2003; pp. 253-266; vol. 3; Nat Rev Cancer.
F.G. Larsen et al.,; "CpG islands as gene markers in the human genome." Journal; 1992; pp. 1095-1107; vol. 13; Genomics.
P.K. Magnusson et al.,; "Genetic link to cervical tumours." Journal; 1999; p. 29-30; Nature.
Ardhendu B. Mitra; "Genetic deletion and human papillomavirus infection in cervical cancer . . . "; Journal; 1999; pp. 322-324; Int J Cancer, Wiley-Liss, Inc.
A. B. Mitra et al.,; "i(5p) and del(6q) are nonrandom abnormalities in carcinoma cervix uteri . . . "; Journal; 1994; pp. 56-58; Cancer Genet Cytogenet.
A.B. Mitra et al.,; (1994). "Allelotype analysis of cervical carcinoma."; Journal; 1994; pp. 4481-4487; Cancer Res.
Michael R. Mullokandov et al.,;"Genomic alterations in cervical carcinoma . . . "; Journal; Jan. 1, 1996; pp. 197-206; Cancer Research.
Masaki Okano et al.,; DNA methyltransferases Dnmt3a and Dnmt3b are essential for de novo methylation and mammalian development; Journal; Oct. 29, 1999; pp. 247-257; vol. 99; Cell Press.
Chandrika J. Piyathilake et al.,; "Folate is associated with the natural history of high-risk human papillomaviruses."; Journal; Dec. 1, 2004; pp. 8788-8793; Cancer Research.
J.S. Rader et al.,; "Allelotyping of all chromosomal arms in invasive cervical cancer."; Journal; 1996; pp. 2737-2741; Oncogene.

(Continued)

*Primary Examiner*—Sarae Bausch
(74) *Attorney, Agent, or Firm*—WPAT, P.C.; Anthony King

(57) ABSTRACT

A method for screening cancer comprises the following steps: (1) providing a test specimen; (2) detecting the methylation state of the CpG sequence in at least one target gene within the genomic DNA of the test specimen, wherein the target genes is consisted of SOX1, PAX1, LMX1A, NKX6-1, WT1 and ONECUT1; and (3) determining whether there is cancer or cancerous pathological change in the specimen based on the presence or absence of the methylation state in the target gene; wherein method for detecting methylation state is methylation-specific PCR (MSP), quantitative methylation-specific PCR (QMSP), bisulfite sequencing (BS), microarrays, mass spectrometer, denaturing high-performance liquid chromatography (DHPLC), and pyrosequencing.

7 Claims, 6 Drawing Sheets

OTHER PUBLICATIONS

Marie-France Robert et al.,; "DNMT1 is required to maintain CpG methylation and aberrant gene silencing in human cancer cells."; Journal; Jan. 2003; pp. 61-65; vol. 33; Nature Genetics.

K.J. Syrjanen; Spontaneous evolution of intraepithelial lesions according to the grade and type of the implicated human papillomavirus (HPV); Journal; 1996; pp. 45-53; Eur J Obstet Gynecol Reprod Biol.

K. Syrjanen et al.,; (1985). "Natural history of cervical human papillomavirus (HPV) infections based on prospective follow-up."; Journal; Nov. 1985; pp. 1086-1092; vol. 92; British Journal Obstetrics and Gynaecology.

J. M. M. Walboomers et al.,; "Human papillomavirus is a necessary cause of invasive cervical cancer worldwide."; Journal; 1999; pp. 12-19; Journal of Pathology; John Wiley & Sons, Ltd.

Nathalie Ylitalo et al.,; "Smoking and oral contraceptives as risk factors for cervical carcinoma in situ."; Journal; 1999; pp. 357-365; Int J Cancer; Wiley-Liss Inc.

Noathalie Ylitalo et al.,; (2000). "Consistent high viral load of human papillomavirus 16 and risk of cervical carcinoma in situ..."; Journal; Jun. 24, 2000; pp. 2194-2198; vol. 355; The Lancet.

Harald Zur Hausen; Papillomaviruses causing cancer: evasion from host-cell control in early events in carcinogenesis.; Journal; May 3, 2000; pp. 690-698; vol. 92, No. 9; Journal of the National Cancer Institute.

Patrik K.E. Magnusson et al.,; Cervical cancer risk: is there a genetic component?; Journal; Apr. 2000; pp. 145-148; vol. 6; Molecular Medicine Today; Elsevier Science Ltd.

* cited by examiner

```
                        SEQUENCE LISTING

<160> NUMBER OF SEQ ID NOS: 58

<210> SEQ ID NO 1
<211> LENGTH: 2300
<212> TYPE: DNA
<213> ORGANISM: Homo sapiens

<400> SEQUENCE: 1
tctccacaag cactctcatc tcagggtgcc tcggggaggg cagaggagga atacttgggc      60
tcaaaagtcg tctttggacc actttcagat cagtctggtg gaaacggtag tgtgagcgct     120
atgctacttg agactgcgtt tgaaaatctc tttcacgttc ccaaatcaaa gccactttga     180
ggtttaagaa tgataaccac aggtgaatgc cttactcttt ccacgagcca ggcctttcct     240
ttgcatgacg cagaccggcg gctgagaccc gtcctgaggc cccgcctttc attcggttta     300
tgtggccccg cgcagttcac gcagttttct ccgttcttag gcaaccagct cgtgggaaat     360
tcactccaga aaagcgtgcg ccatatcatt attttgcgat tcaacaaact ttttcaactg     420
ttgttcagga actagattcc agatagatct tgttgtgttc ggccttccta gaaattcctt     480
ttccagagga agaagatccg ggttgggaag agtgcgtgac tatggccccg ggctcattga     540
aagactcctc cccacaaaag tttagggctg atactaaacg aagctatgga gccatgccca     600
cacaaatact cccccttac ccgaattgtg gggcctggac tgtgaaggcc ttcgctgcaa      660
gagcgggcac tggcgaactt cagtgcacgc cgcggccgag aacggatgca gggcggggga     720
tggctgagcc gcctgatcct tgcagagaac ctgcagggc cctcggaggg tatccctgc      780 gtccaaggga gcgcccctcc ttttcagcac tcggggaac tgagggcgac gtgccagccc      840
cgcactcaac tttccccttc cctgcaggca cagagttggc cggcggggc agaggaggag      900 ctgggtctcc actgcgcccg tttaaacctg gccaggggct gcgtttcctc cccccacccc     960
acgacgatcc tttcttagtc ttcgcttttc aacccaatcg ttaatcattc ggaacgcgcg    1020
ggcggggagc ggcgaggagg gcgagctcgg ggttcgccgc cgccgccgcc gccgcgcgcg    1080
cgcgctcagg aagcggtgtg gctgtcaccc cctcccgggc ctcctccccc ctccttcctg    1140
ctttgctccc cctccttcct ccctcctcc ccgctccgcc gcccgcgccc agtgtatcta     1200
ctccctcccc acgtcactcg ccagcgcgcc atgcaaatca ccgccgccgc cggctcccat    1260
tggccgcggc gcgctcattt aatggcagcc cgggcccggc gtatggctgc tgggccccgc    1320
gcgccgccgg ccccgcgtgc gcctccgctc cgagcgcacg gccccgggca ggcagcgggc    1380
```

```
agcccatccc gggctcggcg gccccggctc tccggccctc tccgcgagcc cgcgctcctc    1440
ccgctgtccc cgggcccctc cctggctgca ccgtaatcgc ccctgcagg ccccctgcg      1500 cctccccccc cccgccactg gcgcctggct tcccccgggc acctgggacc agcacatgcc    1560
cagcgcacgc ggcgcgccgc cctgctagaa gttgcagcct ccgagttgga ggccgctgag    1620
gaccgagcgc aggaggaagg agacagcgcg cagcggcggc cggcgaggag acagcacacc    1680
ccgggccggg cccagcgcac cgctcccggc cccaaaagcg gagctgcaac ttggccacga    1740
ctgcacctgt ttgcaccgct ccgccgaggg cgcctgggct gcggtggcgg cgaagacggc    1800
gaccccgacc gtcggcctct ttggcaagtg gtttgtgcat caggagaaac tttccacctg    1860
cgagccgaac cggcgccgag tgcgtgtgtt tctgcctttt tttgttgtcg ttgcctccac    1920
ccctccccat tcttctctcc gctaggaccc ccccgccccc gtctcactcc gtctgaattc    1980
ctctccgtct ccctcccacc ccggccgtct atgctccagg ccctctcctc gcggtgccgg    2040
tgaacccgcc agccgccccg atgtacagca tgatgatgga gaccgacctg cactcgcccg    2100
gcggcgccca ggccccacg aacctctcgg gccccgccgg ggcggcggc ggcggggggcg     2160 gaggcggggg cggcggcggc ggcggggggcg ccaaggccaa ccaggaccgg gtcaaacggc   2220
ccatgaacgc cttcatggtg tggtcccgcg ggcagcggcg caagatggcc caggagaacc    2280
ccaagatgca caactcggag                                                2300

<210> SEQ ID NO 2
<211> LENGTH: 1200
<212> TYPE: DNA
<213> ORGANISM: Homo sapiens

<400> SEQUENCE: 2
agaaagacga ggccaggcca cctgggatag agtggtgcga gattccaccg ccagggagaa      60
aggaacttgt ccttcagacc tagagctgga gctatgcatt tggcctcccg ccggtcgcgc     120
ttggggacag gagggcgccg gatctatgcg ccccttagca gcagatcggg atccttttgc     180
ctcctgcccc ttctgtcact gcttggagag ggatgagttc tggtggctgg gcctggctgt     240
aggagacagg atttggaccg tgcccctctc gcatcaccga aatcacccc actattccaa      300 gagtggttgg ctattaaacg tgaagatttc ctgagagaag gattgaggac ctggccagga     360
atgggacaca agttccgcct tgtgtcttcc tgacaggagc cctgcaccgc gctggacgct     420
caccttgaca ctcccagcca gctggggtac tgatcccacc cttccccggc cgctgccccg     480
ggagtgggga ggtagagaga gccacacccg aaacacctt ccacgataaa cttttattct      540
ctatcttatt attaatggtg gcggaaataa aactaaaacc aaaacgaaaa cgagtactag     600
tactaacaca ctaatcaatt tgagatgact tccccctcat tcccaaagct agaggaggaa     660
gggggctgaa aggggctcag agcagtggaa ggtcccaggc ccagctgggg ttgggacgtg     720
tgtgtgtgtg tgtgtgtgtg tgtgtgtgtg tgtgtgtgtg tagaggggtg ggttccgggg     780
gggtggtgga agagggccga gggggagga tagaaggagg gggtagagtt tcagggcggg     840
gaggggggcg ctgggcgca gtgacgggaa ccaatgagct gccaactcgc gcgtctccgg     900
cgtgactgcc gagattgacg tggaggacac gtcaaattga ttcccgcacg ctgcagcctc    960
ccggtcagac gaatttctcc caatcggatg aagttcaccc tgggcctggg gtcgcgggcg    1020
tggagagtgt cctgggaggg ggcagcagcg gcggcggcag gccctggagc gggcggcagc    1080
gcgctccgct gccgcgcaca gcgcgtctcc agcccgcggc tgggccgccg cggctctcgg    1140
```

-continued

```
ctctcgggcg ccctccctct atgcctctca cgcggcggcg gcggcgccca agctctcccg    1200
```

<210> SEQ ID NO 3
<211> LENGTH: 2350
<212> TYPE: DNA
<213> ORGANISM: Homo sapiens

<400> SEQUENCE: 3

```
agcccccgc  ccagcgcacc ccacccctc  tccgccgccg cgcacgcagc gccgcggccc     60
ctgtcagaag ctgcaggatc cgccccggcg aagcagggcc gactcgcacc caggaccctg    120
ggcctctgcc ttccctccta gccttggaga agcaactggc cctctcctcc cgctgaggag    180
cgacgcgggc tggtaggacg tcccgggaag gccggcagct cgcgaccacg tcccggccca    240
gcctgggcgc gccgaggagc agagccagcg gccggcgttc gctccggctc cctccccggc    300
gctccgaagc cgagggcggc tcctccggct gcagtctcgg gggcgacgcc ttcccgggca    360
gaagcttcca gcagcgctcc gcaacttctc tctgctccag tcactgggag agagctcgcc    420
taccaggtaa gtaaggctgc ccgtgcctag gctgtggctc gggcgggcgt gtttctgaaa    480
gttgacttga aatgcatcca agagtgagcc gggccagccg ggctcctcc  ccgaggcgac    540
tcttttgctt ctgcagacat tcccggcact ggccgactgg cgggaggacc tccccgcgcg    600
ccccgcacac cggctcctgc gcgcacccca acagagcgca cgccaggag  tccagaagcg    660
ggcgggacgc cctccgggtc ccttacagtg cccctctcg acctggggca ggtgagggcc    720
gcaacggggc ggctgggacg cgggattgca aaccccatcg tcccgcgtgc ctggacccgg    780
tcgctcgagg gagggtaccc actctttata tacccaatat accccagtag ctgcgttcct    840
gcagagacgt cccgagggcc caccttcgta taggttgggg cggagtcgga ttcgggatgg    900
aaaacctggg gcaagggatg taggtggggg tgagggggc  aggagaagga gaaacgcagt    960
tgggggcgg  aggcctaagt acataacgtg ttgacttcaa gtgaaatcag atcagccaga   1020
gcagttcgct gtgactgatc tcctcccca ccctacattc tcttggctgg accctatcct   1080
cctggctgat tctggtcgcc ctggacactc cctcagttct ttcccaggag tgcggtggct   1140
gctggcgccg agtcccagcg ggcacggacg tcagacgcat cgtttcttct cctctacagg   1200
tcctcccggc ccggcccgaa catgctggac ggcctaaaga tggaggagaa cttccaaagc   1260
gcgatcgaca cctcggcctc cttctcctcg ctgctgggtg agtgttcagg ccgtgcgtcc   1320
tgggcgcact ctctttccgc ttggcgctga gctctggagc ccgctctct  gggacctggt   1380
ccgcgatagg gaagctagcg ccctcttca  tacactaaat tgagcccat  cactatctgt   1440
ccgtcagtgc ttgtgggtcg tccctaccca aataaatcca acaagccgcc ccaggcctca   1500
cgcactgggc accgaattcc ccaaagccgc gaggggcggg cgagcttgtt cgtaggcgtc   1560
tgagtggcaa gtgattaaaa atacccaggg ctggattttt aatctcggag ctgatcgacg   1620
tctcataaat gccgccctct tctcgcggcc tagaggcaat agcatccgag acccgaggcc   1680
tggagcgccc aagttcgagg aggcttctct cccccaccaa ctccagcccc aatttcagcc   1740
atgggcaagg ccgagagaga cttttctggg ccagtaggca acgcagcgcg gggattagac   1800
cgcgcggctg ggccctaggc tccgcgttaa ttaactggag ctggatgtcg ggtcctgtgg   1860
gtccccctc  acaactcctt tgcagcgaca gaggaggagc agcgagtcaa ggaccccgga   1920
agagtgtcca cacacgggtc ttgcagagct gaagccagag attctggtta cggctccccc   1980
acccactctg cccttggagc ttttcaagtt tgggaagccc gtatttattt ttatttattt   2040
ttatttattt attttagca  ggagggagtt ttccttctgt cctttaaacc tcttgcctct   2100
```

```
ttcactcgga accgctagag cggcatgaat gtggaggatg agacagttct gctggagaaa    2160
ccaaatccag tgaggaatct ccccaccccc aacaccctag atgaaacgaa atcacgtgca    2220
ctgagcgccc ctctttgaac cccccttccg ggaacttttg gacttgccca gcctcggaag    2280
agagcggaag ccagagcagg cagtacccgg gcgggcagcg ggtgcggatt tatgtataca    2340
gcgggcgtcg                                                           2350
```

<210> SEQ ID NO 4
<211> LENGTH: 1250
<212> TYPE: DNA
<213> ORGANISM: Homo sapiens

<400> SEQUENCE: 4

```
aaagagcgga ggagccgcgg agagggtcag tttggccaga ggacaggact tagaagaccg     60
aagcctggga agccgcgaag aaaatgccag agaggagagt caaaggctga gagtgagagg    120
gagagaggga gcgggggtgg ggcggggtc gccgggcccg tttgcagaag tggactgacg    180
agcggcgccg aaacccagcc gtcagacttt tcacacttag tcttttgttt ttctgtgttt    240
ttcctccccc tttttctttt caatattgca actccagtgc cccgtgggcc agagggcaag    300
gcgggtggag gtgaggacct gggagccgcg gggatccgtg gcactgccct ttctggcgca    360
gcagcccggg gcagcgtggg cggaggaagc ccgcacagag gctagatctc ccgcgggctg    420
gatgcgcttt ctccccggc acagtgagcg tcgaatgcga atcagccgcg cgaccgaaag    480
agcagagcat cccagtaaga tcagaggagc gccacgggct gcacaaggcg tcctttgaac    540
ctccccaaag aaagcaagcc accccacc tccaacttca aagtggagat tcggcaacta    600
actttgctac aaactctccg gagccagcct gggttttgtt ttgcttatt cccggggca    660 gaagatgaga agtagcgcac tttgaacagc taggaaaagt gaggaagaga gaatagccag    720
ggatcgaatc taggactcgc ggaacgaaag gactgcctag cccgccggga cgcctgcttt    780
tctcggcgag ctgccgcctc ccgcgtggag ggtttggaca tctctgctgc gcagctaggc    840
gagcaactcc cggcagcggc attttttggtt cagttggcag ctcgcctccg ggcgcgccga    900
gtgcctctcc gctcgcgccc tcggcgcttc cggctcctct gagccccgcg gggggcacca    960
gccagcgccc tcgctgcaag gctacggtct ccggcgtggc cgtgggatgt tagcggtggg   1020
ggcaatggag ggcacccggc agagcgcatt cctgctcagc agccctcccc tggccgccct   1080
gcacagcatg gccgagatga agaccccgct gtaccctgcc gcgtatcccc cgctgcctgc   1140 cggcccccc tcctcctcgt cctcgtcgtc gtcctcctcg tcgccctccc cgcctctggg   1200
cacccacaac ccaggcggcc tgaagccccc ggccacgggg gggctctcat             1250
```

<210> SEQ ID NO 5
<211> LENGTH: 1700
<212> TYPE: DNA
<213> ORGANISM: Homo sapiens

<400> SEQUENCE: 5

```
tcactgagca accagaatgg tatcctcgac cagggccaca ggcagtgctc ggcggagtgg     60
ctccaggagt tacccgctcc ctgccgggct tcgtatccaa accctcccct tcacccctcc    120
tccccaaact gggcgccagg atgctccggc cggaatatac gcaggctttg gcgtttgcc    180 caagggtttt cttccctcct aaactagccg ctgttttccc ggcttaaccg tagaagaatt    240
agatattcct cactggaaag ggaaactaag tgctgctgac tccaattta ggtaggcggc    300
```

```
aaccgccttc cgcctggcgc aaacctcacc aagtaaacaa ctactagccg atcgaaatac      360
gcccggctta taactggtgc aactcccggc cacccaactg agggacgttc gctttcagtc      420
ccgacctctg gaacccacaa agggccacct cttttccccag tgaccccaag atcatggcca     480
ctcccctacc cgacagttct agaagcaaga gccagactca agggtgcaaa gcaagggtat      540
acgcttcttt gaagcttgac tgagttcttt ctgcgctttc ctgaagttcc cgccctcttg      600
gagcctacct gcccctccct ccaaaccact cttttagatt aacaacccca tctctactcc      660
caccgcattc gaccctgccc ggactcactg cttacctgaa cggactctcc agtgagacga      720
ggctcccaca ctggcgaagg ccaagaaggg gaggtggggg gagggttgtg ccacaccggc      780
cagctgagag cgcgtgttgg gttgaagagg agggtgtctc cgagagggac gctccctcgg      840
acccgccctc accccagctg cgagggcgcc cccaaggagc agcgcgcgct gcctggccgg      900
gcttgggctg ctgagtgaat ggagcggccg agcctcctgg ctcctcctct tccccgcgcc      960 gccgcccct cttatttgag ctttgggaag ctgagggcag ccaggcagct ggggtaagga     1020
gttcaaggca gcgcccacac ccgggggctc tccgcaaccc gaccgcctgt ccgctccccc     1080
acttcccgcc ctccctccca cctactcatt caccccaccca cccacccaga gccgggacgg     1140
cagcccaggc gcccgggccc cgccgtctcc tcgccgcgat cctggacttc ctcttgctgc     1200
aggaccccgg ttccacgtgt gtccggagc cggcgtctca gcacacgctc cgctccgggc     1260
ctgggtgcct acagcagcca gagcagcagg gagtccggga cccgggcggc atctgggcca     1320
agttaggcgc cgccgaggcc agcgctgaac gtctccaggg ccggaggagc cgcggggcgt     1380
ccgggtctga gccgcagcaa atgggctccg acgtgcggga cctgaacgcg ctgctgcccg     1440
ccgtcccctc cctgggtggc ggcggcggct gtgccctgcc tgtgagcggc gcggcgcagt     1500
gggcgccggt gctggacttt gcgccccgg gcgcttcggc ttacgggtcg ttgggcggcc     1560
ccgcgccgcc accggctccg ccgccacccc cgccgccgcc gcctcactcc ttcatcaaac     1620
aggagccgag ctggggcggc gcggagccgc acgaggagca gtgcctgagc gccttcactg     1680 tccactttc cggccagttc                                                  1700
```

<210> SEQ ID NO 6
<211> LENGTH: 1850
<212> TYPE: DNA
<213> ORGANISM: Homo sapiens

<400> SEQUENCE: 6

```
gaaagaaagc cgcggcatgt ggcggccggg tgtacgtctc aaactggggg cctccgcaca       60
cgtccccacc aggcccaaag accaggttcg attccagatt ggagcgtgac tgtgggaagg      120
gcgaaattac tcccgaagct gaattgattt tcaaatctgg aggcgtctct cggggacgcc      180
gggaaaaggg cgtccctagg ggccaagcgg agacccgcgc gccggcgtcc accctgtctg      240
cgtcagtact tctggaaagc aaccgcctcc gggtgcttta gcaggagggc cttgggagta      300
accgcaggga cggcccgagc ctccacggcc ccaccagcac ccggaagtta acatgggtac      360
cctccagggc actccctccg ctctccctcg ccccctccca caggccgagt catcggcgaa      420
gcggacgcac agccttaatt atgagctgag cgggagaagg agccaggcgg cggggggacag     480 tgaggtatgg cccgaactgg gattcttggc actgattact cctctcccca ggcatggat      540 gagaaagggt gggcaagtat gtatctggga ggacgaaggg tgccgggtca acggccgcca      600
aacggaccca gcccttaag caatctgcac cccaccccac cccaaccccc atcccccaat      660
aggccgtgaa ttcaagggtg ggaaagcgca ctcccagcag ccccccggga aataaagctt      720
```

-continued

```
agtgggctag agccgaaggg gtgatgacac agtccccagc tccccgggca agctgcaccg    780
ggaagcagca actggagaga gagggggcgat gtctccaagc acagcactcc agccgctaga    840
agcccgacac gagcgtcccc gggctgggag gacagagccc actcaagcaa gggaggcgag    900
cgagccaggc gcgagtctcc tgggattgca gcggcggccc caggtcgcgc tctgcgccaa    960
tctttcgcac gtgcccgcag ctccctggcc atccagcgcc gcagggaagg cgctgggccc    1020
cctccttcat ttgtaccggg acgccaaggg cctggcgcgc gcgacctag ggggcggggg    1080 cgggcctcgc gcatgcgcgc tgcgcctggc gggcgtgagg gcgggccgct gcggcggcgg    1140
cggcggcggc taccgaaccg cggccacaga gtctgtaaca gtaacagagc catggctcaa    1200
gctggccagc ggggcgggca ggcagcagac gcggcaggcg cgcgggccgc ggcaggggag    1260
ccggagacct cagaattta gaaagagag gggcgagagg tggccgaggc gggcgggctg    1320
gggcactgcg ctctcccaac ggcgcggatc ctctttggaa attaatatta aaaaaaaaaa    1380
agccgaggac gcagagggga aggtgggggg taagagggaa ggcgagacac acacacacac    1440
acacacgcac acgcacacac ggacacacac acacggagag agagagagag agagacagag    1500
ccccacagtg agaggaagga aggcaacagt cgccagcagc cgatgtgaag accggactcc    1560
gtgcgcccct cgccgcctct gcctggccac atcgatgttg tgtccgccgc ctgctcgccc    1620
ggatcacgat gaacgcgcag ctgaccatgg aagcgatcgg cgagctgcac ggggtgagcc    1680
atgagccggt gcccgcccct gccgacctgc tgggcggcag ccccacgcg cgcagctccg    1740 tggcgcaccg cggcagccac ctgccccccg cgcacccgcg ctccatgggc atggcgtccc    1800
tgctggacgg cggcagcggc ggcggagatt accaccacca ccaccgggcc           1850
```

<210> SEQ ID NO 7
<211> LENGTH: 24
<212> TYPE: DNA
<213> ORGANISM: artificial sequence
<220> FEATURE:
<223> OTHER INFORMATION: A forward primer for amplifying the methylated
      SOX1 gene sequence, the primer was synthesized by 3900 High-
      Throughput DNA Synthesizer and Accessories (ABI, Applied
      Biosystems, USA) and purified by PolyAcrylamide Gel
      Electrophoresis (PAGE).

<400> SEQUENCE: 7 cgttttttttt ttttcgttat tggc                                          24

<210> SEQ ID NO 8
<211> LENGTH: 20
<212> TYPE: DNA
<213> ORGANISM: artificial sequence
<220> FEATURE:
<223> OTHER INFORMATION: A reverse primer for amplifying the methylated
      SOX1 gene sequence, the primer was synthesized by 3900 High-
      Throughput DNA Synthesizer and Accessories (ABI, Applied
      Biosystems, USA) and purified by PolyAcrylamide Gel
      Electrophoresis (PAGE).

<400> SEQUENCE: 8
cctacgctcg atcctcaacg                                                20

<210> SEQ ID NO 9
<211> LENGTH: 25
<212> TYPE: DNA
<213> ORGANISM: artificial sequence
<220> FEATURE:
<223> OTHER INFORMATION: A forward primer for amplifying the
      unmethylated SOX1 gene sequence, the primer was synthesized by 3900 High-Throughput DNA Synthesizer and Accessories (ABI,
Applied Biosystems, USA) and purified by PolyAcrylamide Gel
Electrophoresis (PAGE).

<400> SEQUENCE: 9 tgttttttttt ttttttgttat tggtg                                25

<210> SEQ ID NO 10
<211> LENGTH: 22
<212> TYPE: DNA
<213> ORGANISM: artificial sequence
<220> FEATURE:
<223> OTHER INFORMATION: A reverse primer for amplifying the
      unmethylated SOX1 gene sequence, the primer was synthesized by
      3900 High-Throughput DNA Synthesizer and Accessories (ABI,
      Applied Biosystems, USA) and purified by PolyAcrylamide Gel
      Electrophoresis (PAGE).

<400> SEQUENCE: 10
cctacactca atcctcaaca ac                                     22

<210> SEQ ID NO 11
<211> LENGTH: 18
<212> TYPE: DNA
<213> ORGANISM: artificial sequence
<220> FEATURE:
<223> OTHER INFORMATION: A forward primer for amplifying the
      methylated LMX1A gene sequence, the primer was synthesized by
      3900 High-Throughput DNA Synthesizer and Accessories (ABI,
      Applied Biosystems, USA) and purified by PolyAcrylamide Gel
      Electrophoresis (PAGE).

<400> SEQUENCE: 11
tttagaagcg ggcgggac                                          18

<210> SEQ ID NO 12
<211> LENGTH: 17
<212> TYPE: DNA
<213> ORGANISM: artificial sequence
<220> FEATURE:
<223> OTHER INFORMATION: A reverse primer for amplifying the methylated
      LMX1A gene sequence, the primer was synthesized by 3900 High-
      Throughput DNA Synthesizer and Accessories (ABI, Applied
      Biosystems, USA) and purified by PolyAcrylamide Gel
      Electrophoresis (PAGE).

<400> SEQUENCE: 12
ccgaatccaa acacgcg                                           17

<210> SEQ ID NO 13
<211> LENGTH: 22
<212> TYPE: DNA
<213> ORGANISM: artificial sequence
<220> FEATURE:
<223> OTHER INFORMATION: A forward primer for amplifying the
      unmethylated LMX1A gene sequence, the primer was synthesized by
      3900 High-Throughput DNA Synthesizer and Accessories (ABI,
      Applied Biosystems, USA) and purified by PolyAcrylamide Gel
      Electrophoresis (PAGE).

<400> SEQUENCE: 13
gagtttagaa gtgggtggga tg                                     22

<210> SEQ ID NO 14
<211> LENGTH: 24
<212> TYPE: DNA
<213> ORGANISM: artificial sequence
<220> FEATURE:
<223> OTHER INFORMATION: A reverse primer for amplifying the unmethylated LMX1A gene sequence, the primer was synthesized by
3900 High-Throughput DNA Synthesizer and Accessories (ABI,
Applied Biosystems, USA) and purified by PolyAcrylamide Gel
Electrophoresis (PAGE).

<400> SEQUENCE: 14
caaccaaatc caaacacaca aaac                                          24

<210> SEQ ID NO 15
<211> LENGTH: 21
<212> TYPE: DNA
<213> ORGANISM: artificial sequence
<220> FEATURE:
<223> OTHER INFORMATION: A forward primer for amplifying the
methylated ONECUT1 gene sequence, the primer was synthesized
by 3900 High-Throughput DNA Synthesizer and Accessories (ABI,
Applied Biosystems, USA) and purified by PolyAcrylamide Gel
Electrophoresis (PAGE).

<400> SEQUENCE: 15
ttgtagcggc ggttttaggt c                                             21

<210> SEQ ID NO 16
<211> LENGTH: 20
<212> TYPE: DNA
<213> ORGANISM: artificial sequence
<220> FEATURE:
<223> OTHER INFORMATION: A reverse primer for amplifying the
methylated ONECUT1 gene sequence, the primer was synthesized by
3900 High-Throughput DNA Synthesizer and Accessories (ABI, Applied
Biosystems, USA) and purified by PolyAcrylamide Gel
Electrophoresis (PAGE).

<400> SEQUENCE: 16
gccaaaccct taacgtcccg                                               20

<210> SEQ ID NO 17
<211> LENGTH: 24
<212> TYPE: DNA
<213> ORGANISM: artificial sequence
<220> FEATURE:
<223> OTHER INFORMATION: A forward primer for amplifying the
unmethylated ONECUT1 gene sequence, the primer was synthesized by
3900 High-Throughput DNA Synthesizer and Accessories (ABI,
Applied Biosystems, USA) and purified by PolyAcrylamide Gel
Electrophoresis (PAGE).

<400> SEQUENCE: 17
gattgtagtg gtggttttag gttg                                          24

<210> SEQ ID NO 18
<211> LENGTH: 25
<212> TYPE: DNA
<213> ORGANISM: artificial sequence
<220> FEATURE:
<223> OTHER INFORMATION: A reverse primer for amplifying the
unmethylated ONECUT1 gene sequence, the primer was synthesized
by 3900 High-Throughput DNA Synthesizer and Accessories (ABI,
Applied Biosystems, USA) and purified by PolyAcrylamide Gel
Electrophoresis (PAGE).

<400> SEQUENCE: 18
caccaaaccc ttaacatccc aatac                                         25

<210> SEQ ID NO 19
<211> LENGTH: 20
<212> TYPE: DNA
<213> ORGANISM: artificial sequence
<220> FEATURE:

<223> OTHER INFORMATION: A forward primer for amplifying the methylated
      PAX1 gene sequence, the primer was synthesized by 3900 High-
      Throughput DNA Synthesizer and Accessories (ABI, Applied
      Biosystems, USA) and purified by PolyAcrylamide Gel
      Electrophoresis (PAGE).

<400> SEQUENCE: 19
tattttgggt ttggggtcgc                                            20

<210> SEQ ID NO 20
<211> LENGTH: 18
<212> TYPE: DNA
<213> ORGANISM: artificial sequence
<220> FEATURE:
<223> OTHER INFORMATION: A reverse primer for amplifying the methylated
      PAX1 gene sequence, the primer was synthesized by 3900 High-
      Throughput DNA Synthesizer and Accessories (ABI, Applied
      Biosystems, USA) and purified by PolyAcrylamide Gel
      Electrophoresis (PAGE).

<400> SEQUENCE: 20
cccgaaaacc gaaaaccg                                              18

<210> SEQ ID NO 21
<211> LENGTH: 24
<212> TYPE: DNA
<213> ORGANISM: artificial sequence
<220> FEATURE:
<223> OTHER INFORMATION: A forward primer for amplifying the
      unmethylated PAX1 gene sequence, the primer was synthesized by
      3900 High-Throughput DNA Synthesizer and Accessories (ABI,
      Applied Biosystems, USA) and purified by PolyAcrylamide Gel
      Electrophoresis (PAGE).

<400> SEQUENCE: 21
gtttattttg ggtttggggt tgtg                                       24

<210> SEQ ID NO 22
<211> LENGTH: 21
<212> TYPE: DNA
<213> ORGANISM: artificial sequence
<220> FEATURE:
<223> OTHER INFORMATION: A reverse primer for amplifying the
      unmethylated PAX1 gene sequence, the primer was synthesized by
      3900 High-Throughput DNA Synthesizer and Accessories (ABI,
      Applied Biosystems, USA) and purified by PolyAcrylamide Gel
      Electrophoresis (PAGE).

<400> SEQUENCE: 22
cacccaaaaa ccaaaaacca c                                          21

<210> SEQ ID NO 23
<211> LENGTH: 20
<212> TYPE: DNA
<213> ORGANISM: artificial sequence
<220> FEATURE:
<223> OTHER INFORMATION: A forward primer for amplifying the
      methylated NKX6.1 gene sequence, the primer was synthesized by
      3900 High-Throughput DNA Synthesizer and Accessories (ABI,
      Applied Biosystems, USA) and purified by PolyAcrylamide Gel
      Electrophoresis (PAGE).

<400> SEQUENCE: 23
cgtggtcgtg ggatgttagc                                            20

<210> SEQ ID NO 24
<211> LENGTH: 21
<212> TYPE: DNA
<213> ORGANISM: artificial sequence
<220> FEATURE:
<223> OTHER INFORMATION: A reverse primer for amplifying the
     methylated NKX6.1 gene sequence, the primer was synthesized by
     3900 High-Throughput DNA Synthesizer and Accessories (ABI,
     Applied Biosystems, USA) and purified by PolyAcrylamide Gel
     Electrophoresis (PAGE).

<400> SEQUENCE: 24
acaaacaacg aaaaatacgc g                                                 21

<210> SEQ ID NO 25
<211> LENGTH: 22
<212> TYPE: DNA
<213> ORGANISM: artificial sequence
<220> FEATURE:
<223> OTHER INFORMATION: A forward primer for amplifying the
     unmethylated NKX6.1 gene sequence, the primer was synthesized by
     3900 High-Throughput DNA Synthesizer and Accessories (ABI,
     Applied Biosystems, USA) and purified by PolyAcrylamide Gel
     Electrophoresis (PAGE).

<400> SEQUENCE: 25
gtgtggttgt gggatgttag tg                                                22

<210> SEQ ID NO 26
<211> LENGTH: 25
<212> TYPE: DNA
<213> ORGANISM: artificial sequence
<220> FEATURE:
<223> OTHER INFORMATION: A reverse primer for amplifying the
     unmethylated NKX6.1 gene sequence, the primer was synthesized by
     3900 High-Throughput DNA Synthesizer and Accessories (ABI,
     Applied Biosystems, USA) and purified by PolyAcrylamide Gel
     Electrophoresis (PAGE).

<400> SEQUENCE: 26
caacaaacaa caaaaaatac acaac                                             25

<210> SEQ ID NO 27
<211> LENGTH: 21
<212> TYPE: DNA
<213> ORGANISM: artificial sequence
<220> FEATURE:
<223> OTHER INFORMATION: A forward primer for amplifying the
     methylated WT1 gene sequence, the primer was synthesized by 3900
     High-Throughput DNA Synthesizer and Accessories (ABI, Applied
     Biosystems, USA) and purified by PolyAcrylamide Gel
     Electrophoresis (PAGE).

<400> SEQUENCE: 27
tgttgagtga atggagcggt c                                                 21

<210> SEQ ID NO 28
<211> LENGTH: 23
<212> TYPE: DNA
<213> ORGANISM: artificial sequence
<220> FEATURE:
<223> OTHER INFORMATION: A reverse primer for amplifying the
     methylated WT1 gene sequence, the primer was synthesized by 3900
     High-Throughput DNA Synthesizer and Accessories (ABI, Applied
     Biosystems, USA) and purified by PolyAcrylamide Gel
     Electrophoresis (PAGE).

<400> SEQUENCE: 28
cgaaaaaccc ccgaatataa acg                                               23

<210> SEQ ID NO 29
<211> LENGTH: 24
<212> TYPE: DNA

```
<213> ORGANISM: artificial sequence
<220> FEATURE:
<223> OTHER INFORMATION: A forward primer for amplifying the
      unmethylated WT1 gene sequence, the primer was synthesized by
      3900 High-Throughput DNA Synthesizer and Accessories (ABI,
      Applied Biosystems, USA) and purified by PolyAcrylamide Gel
      Electrophoresis (PAGE).

<400> SEQUENCE: 29
gttgttgagt gaatggagtg gttg                                            24

<210> SEQ ID NO 30
<211> LENGTH: 29
<212> TYPE: DNA
<213> ORGANISM: artificial sequence
<220> FEATURE:
<223> OTHER INFORMATION: A reverse primer for amplifying the
      unmethylated WT1 gene sequence, the primer was synthesized
      by 3900 High-Throughput DNA Synthesizer and Accessories (ABI,
      Applied Biosystems, USA) and purified by PolyAcrylamide Gel
      Electrophoresis (PAGE).

<400> SEQUENCE: 30
aattacaaaa aaccccaaa tataaacac                                        29

<210> SEQ ID NO 31
<211> LENGTH: 26
<212> TYPE: DNA
<213> ORGANISM: artificial sequence
<220> FEATURE:
<223> OTHER INFORMATION: A forward bisulfite sequencing primer for SOX1
      gene sequence, the primer was synthesized by 3900 High-Throughput
      DNA Synthesizer and Accessories (ABI, Applied Biosystems, USA)
      and purified by PolyAcrylamide Gel Electrophoresis (PAGE).

<400> SEQUENCE: 31
gttgttttyg ggttttttt tggttg                                           26

<210> SEQ ID NO 32
<211> LENGTH: 28
<212> TYPE: DNA
<213> ORGANISM: artificial sequence
<220> FEATURE:
<223> OTHER INFORMATION: A reverse bisulfite sequencing primer for SOX1
      gene sequence, the primer was synthesized by 3900 High-Throughput
      DNA Synthesizer and Accessories (ABI, Applied Biosystems, USA) and
      purified by PolyAcrylamide Gel Electrophoresis (PAGE).

<400> SEQUENCE: 32
atttctccta atacacaaac cacttacc                                        28

<210> SEQ ID NO 33
<211> LENGTH: 29
<212> TYPE: DNA
<213> ORGANISM: artificial sequence
<220> FEATURE:
<223> OTHER INFORMATION: A forward bisulfite sequencing primer for
      LMX1A gene sequence, the primer was synthesized by 3900 High-
      Throughput DNA Synthesizer and Accessories (ABI, Applied
      Biosystems, USA) and purified by PolyAcrylamide Gel
      Electrophoresis (PAGE).

<400> SEQUENCE: 33
tagttattgg gagagagtty gtttattag                                       29

<210> SEQ ID NO 34
<211> LENGTH: 24
<212> TYPE: DNA
<213> ORGANISM: artificial sequence
```

```
<220> FEATURE:
<223> OTHER INFORMATION: A reverse bisulfite sequencing primer for
      LMX1A gene sequence, the primer was synthesized by 3900 High-
      Throughput DNA Synthesizer and Accessories (ABI, Applied
      Biosystems, USA) and purified by PolyAcrylamide Gel
      Electrophoresis (PAGE).

<400> SEQUENCE: 34
ctaccccaaa tcraaaaaaa acac                                          24

<210> SEQ ID NO 35
<211> LENGTH: 22
<212> TYPE: DNA
<213> ORGANISM: artificial sequence
<220> FEATURE:
<223> OTHER INFORMATION: A forward bisulfite sequencing primer for
      ONECUT1 gene sequence, the primer was synthesized by 3900
      High-Throughput DNA Synthesizer and Accessories (ABI, Applied
      Biosystems, USA) and purified by PolyAcrylamide Gel
      Electrophoresis (PAGE).

<400> SEQUENCE: 35
gagtttattt aagtaaggga gg                                            22

<210> SEQ ID NO 36
<211> LENGTH: 30
<212> TYPE: DNA
<213> ORGANISM: artificial sequence
<220> FEATURE:
<223> OTHER INFORMATION: A reverse bisulfite sequencing primer for
      ONECUT1 gene sequence, the primer was synthesized by 3900 High-
      Throughput DNA Synthesizer and Accessories (ABI, Applied
      Biosystems, USA) and purified by PolyAcrylamide Gel
      Electrophoresis (PAGE).

<400> SEQUENCE: 36
caacttaaac cataactcta ttactattac                                    30

<210> SEQ ID NO 37
<211> LENGTH: 22
<212> TYPE: DNA
<213> ORGANISM: artificial sequence
<220> FEATURE:
<223> OTHER INFORMATION: A forward bisulfite sequencing primer for
      PAX1 gene sequence, the primer was synthesized by 3900 High-
      Throughput DNA Synthesizer and Accessories (ABI, Applied
      Biosystems, USA) and purified by PolyAcrylamide Gel
      Electrophoresis (PAGE).

<400> SEQUENCE: 37
gtgttttggg aggggtagt ag                                             22

<210> SEQ ID NO 38
<211> LENGTH: 21
<212> TYPE: DNA
<213> ORGANISM: artificial sequence
<220> FEATURE:
<223> OTHER INFORMATION: A reverse bisulfite sequencing primer for
      PAX1 gene sequence, the primer was synthesized by 3900 High-
      Throughput DNA Synthesizer and Accessories (ABI, Applied
      Biosystems, USA) and

<400> SEQUENCE: 38
ccctcccraa ccctacctat c                                             21

<210> SEQ ID NO 39
<211> LENGTH: 22
<212> TYPE: DNA
<213> ORGANISM: artificial sequence
```

```
<220> FEATURE:
<223> OTHER INFORMATION: A forward bisulfite sequencing primer for PAX1
      gene sequence, the primer was synthesized by 3900 High-Throughput
      DNA Synthesizer and Accessories (ABI, Applied Biosystems, USA)
      and purified by PolyAcrylamide Gel Electrophoresis (PAGE).

<400> SEQUENCE: 39
gatagaagga gggggtagag tt                                              22

<210> SEQ ID NO 40
<211> LENGTH: 21
<212> TYPE: DNA
<213> ORGANISM: artificial sequence
<220> FEATURE:
<223> OTHER INFORMATION: A reverse bisulfite sequencing primer for PAX1
      gene sequence, the primer was synthesized by 3900 High-Throughput
      DNA Synthesizer and Accessories (ABI, Applied Biosystems, USA)
      and purified by PolyAcrylamide Gel Electrophoresis (PAGE).

<400> SEQUENCE: 40
tactaccccc tcccaaaaca c                                               21

<210> SEQ ID NO 41
<211> LENGTH: 25
<212> TYPE: DNA
<213> ORGANISM: artificial sequence
<220> FEATURE:
<223> OTHER INFORMATION: A forward bisulfite sequencing primer for
      NKX6.1 gene sequence, the primer was synthesized by 3900 High-
      Throughput DNA Synthesizer and Accessories (ABI, Applied
      Biosystems, USA) and purified by PolyAcrylamide Gel
      Electrophoresis (PAGE).

<400> SEQUENCE: 41
ggtatttttg gtttagttgg tagtt                                           25

<210> SEQ ID NO 42
<211> LENGTH: 22
<212> TYPE: DNA
<213> ORGANISM: artificial sequence
<220> FEATURE:
<223> OTHER INFORMATION: A reverse bisulfite sequencing primer for
      NKX6.1 gene sequence, the primer was synthesized by 3900 High-
      Throughput DNA Synthesizer and Accessories (ABI, Applied
      Biosystems, USA) and purified by PolyAcrylamide Gel
      Electrophoresis (PAGE).

<400> SEQUENCE: 42
aataccctcc attaccccca cc                                              22

<210> SEQ ID NO 43
<211> LENGTH: 22
<212> TYPE: DNA
<213> ORGANISM: artificial sequence
<220> FEATURE:
<223> OTHER INFORMATION: A forward bisulfite sequencing primer for
      NKX6.1 gene sequence, the primer was synthesized by 3900
      High-Throughput DNA Synthesizer and Accessories (ABI, Applied
      Biosystems, USA) and purified by PolyAcrylamide Gel
      Electrophoresis (PAGE).

<400> SEQUENCE: 43 ggtggggta atggagggta tt                                               22

<210> SEQ ID NO 44
<211> LENGTH: 24
<212> TYPE: DNA
<213> ORGANISM: artificial sequence
<220> FEATURE:
```

-continued

<223> OTHER INFORMATION: A reverse bisulfite sequencing primer for
NKX6.1 gene sequence, the primer was synthesized by 3900 High-
Throughput DNA Synthesizer and Accessories (ABI, Applied
Biosystems, USA) and purified by PolyAcrylamide Gel
Electrophoresis (PAGE).

<400> SEQUENCE: 44
cctaaattat aaatacccaa aaac                                        24

<210> SEQ ID NO 45
<211> LENGTH: 24
<212> TYPE: DNA
<213> ORGANISM: artificial sequence
<220> FEATURE:
<223> OTHER INFORMATION: A forward bisulfite sequencing primer for WT1
gene sequence, the primer was synthesized by 3900 High-
Throughput DNA Synthesizer and Accessories (ABI, Applied
Biosystems, USA) and purified by PolyAcrylamide Gel
Electrophoresis (PAGE).

<400> SEQUENCE: 45
gtgttgggtt gaagaggagg gtgt                                        24

<210> SEQ ID NO 46
<211> LENGTH: 28
<212> TYPE: DNA
<213> ORGANISM: artificial sequence
<220> FEATURE:
<223> OTHER INFORMATION: A reverse bisulfite sequencing primer for WT1
gene sequence, the primer was synthesized by 3900 High-Throughput
DNA Synthesizer and Accessories (ABI, Applied Biosystems, USA)
and purified by PolyAcrylamide Gel Electrophoresis (PAGE).

<400> SEQUENCE: 46
atcctacaac aaaaaaaaat ccaaaatc                                    28

<210> SEQ ID NO 47
<211> LENGTH: 22
<212> TYPE: DNA
<213> ORGANISM: artificial sequence
<220> FEATURE:
<223> OTHER INFORMATION: A forward RT-RCR primer for SOX1 gene sequence,
the primer was synthesized by 3900 High-Throughput DNA Synthesizer
and Accessories (ABI, Applied Biosystems, USA) and purified by
PolyAcrylamide Gel Electrophoresis (PAGE).

<400> SEQUENCE: 47
agacctagat gccaacaatt gg                                          22

<210> SEQ ID NO 48
<211> LENGTH: 21
<212> TYPE: DNA
<213> ORGANISM: artificial sequence
<220> FEATURE:
<223> OTHER INFORMATION: A reverse RT-RCR primer for SOX1 gene sequence,
the primer was synthesized by 3900 High-Throughput DNA Synthesizer
and Accessories (ABI, Applied Biosystems, USA) and purified by
PolyAcrylamide Gel Electrophoresis (PAGE).

<400> SEQUENCE: 48
gcaccactac gacttagtcc g                                           21

<210> SEQ ID NO 49
<211> LENGTH: 21
<212> TYPE: DNA
<213> ORGANISM: artificial sequence
<220> FEATURE:
<223> OTHER INFORMATION: A forward RT-RCR primer for LMX1A gene
sequence, the primer was synthesized by 3900 High-Throughput DNA Synthesizer and Accessories (ABI, Applied Biosystems, USA) and
purified by PolyAcrylamide Gel Electrophoresis (PAGE).

<400> SEQUENCE: 49
gctgcttctg ctgctgtgtc t                                              21

<210> SEQ ID NO 50
<211> LENGTH: 21
<212> TYPE: DNA
<213> ORGANISM: artificial sequence
<220> FEATURE:
<223> OTHER INFORMATION: A reverse RT-RCR primer for LMX1A gene
      sequence, the primer was synthesized by 3900 High-Throughput DNA
      Synthesizer and Accessories (ABI, Applied Biosystems, USA) and
      purified by PolyAcrylamide Gel Electrophoresis (PAGE).

<400> SEQUENCE: 50
acgtttgggg cgcttatggt c                                              21

<210> SEQ ID NO 51
<211> LENGTH: 21
<212> TYPE: DNA
<213> ORGANISM: artificial sequence
<220> FEATURE:
<223> OTHER INFORMATION: A forward RT-RCR primer for ONECUT1 gene
      sequence, the primer was synthesized by 3900 High-Throughput
      DNA Synthesizer and Accessories (ABI, Applied Biosystems, USA)
      and purified by PolyAcrylamide Gel Electrophoresis (PAGE).

<400> SEQUENCE: 51
caaaccctgg agcaaactca a                                              21

<210> SEQ ID NO 52
<211> LENGTH: 21
<212> TYPE: DNA
<213> ORGANISM: artificial sequence
<220> FEATURE:
<223> OTHER INFORMATION: A reverse RT-RCR primer for ONECUT1 gene
      sequence, the primer was synthesized by 3900 High-Throughput
      DNA Synthesizer and Accessories (ABI, Applied Biosystems, USA)
      and purified by PolyAcrylamide Gel Electrophoresis (PAGE).

<400> SEQUENCE: 52
tgtgttgcct ctatccttcc c                                              21

<210> SEQ ID NO 53
<211> LENGTH: 24
<212> TYPE: DNA
<213> ORGANISM: artificial sequence
<220> FEATURE:
<223> OTHER INFORMATION: A forward RT-RCR primer for PAX1 gene
      sequence, the primer was synthesized by 3900 High-Throughput
      DNA Synthesizer and Accessories (ABI, Applied Biosystems, USA)
      and purified by PolyAcrylamide Gel Electrophoresis (PAGE).

<400> SEQUENCE: 53
cctacgctgc cctacaacca catc                                           24

<210> SEQ ID NO 54
<211> LENGTH: 24
<212> TYPE: DNA
<213> ORGANISM: artificial sequence
<220> FEATURE:
<223> OTHER INFORMATION: A reverse RT-RCR primer for PAX1 gene
      sequence, the primer was synthesized by 3900 High-Throughput DNA
      Synthesizer and Accessories (ABI, Applied Biosystems, USA)
      and purified by PolyAcrylamide Gel Electrophoresis (PAGE).

<400> SEQUENCE: 54

```
tcacgccggc ccagtcttcc atct                                              24

<210> SEQ ID NO 55
<211> LENGTH: 21
<212> TYPE: DNA
<213> ORGANISM: artificial sequence
<220> FEATURE:
<223> OTHER INFORMATION: A forward RT-RCR primer for NKX6.1 gene
      sequence, the primer was synthesized by 3900 High-Throughput
      DNA Synthesizer and Accessories (ABI, Applied Biosystems, USA)
      and purified by PolyAcrylamide Gel Electrophoresis (PAGE).

<400> SEQUENCE: 55
cacacgagac ccactttttc c                                                 21

<210> SEQ ID NO 56
<211> LENGTH: 20
<212> TYPE: DNA
<213> ORGANISM: artificial sequence
<220> FEATURE:
<223> OTHER INFORMATION: A reverse RT-RCR primer for NKX6.1 gene
      sequence, the primer was synthesized by 3900 High-Throughput
      DNA Synthesizer and Accessories (ABI, Applied Biosystems, USA)
      and purified by PolyAcrylamide Gel Electrophoresis (PAGE).

<400> SEQUENCE: 56
cccaacgaat aggccaaacg                                                   20

<210> SEQ ID NO 57
<211> LENGTH: 21
<212> TYPE: DNA
<213> ORGANISM: artificial sequence
<220> FEATURE:
<223> OTHER INFORMATION: A forward RT-RCR primer for WT1 gene sequence,
      the primer was synthesized by 3900 High-Throughput DNA
      Synthesizer and Accessories (ABI, Applied Biosystems, USA)
      and purified by PolyAcrylamide Gel Electrophoresis (PAGE).

<400> SEQUENCE: 57
gctgtcccac ttacagatgc a                                                 21

<210> SEQ ID NO 58
<211> LENGTH: 21
<212> TYPE: DNA
<213> ORGANISM: artificial sequence
<220> FEATURE:
<223> OTHER INFORMATION: A reverse RT-RCR primer for WT1 gene sequence,
      the primer was synthesized by 3900 High-Throughput DNA
      Synthesizer and Accessories (ABI, Applied Biosystems, USA)
      and purified by PolyAcrylamide Gel Electrophoresis (PAGE).

<400> SEQUENCE: 58
tcaaagcgcc agctggagtt t                                                 21
```

CANCER SCREENING METHOD

BACKGROUND OF THE INVENTION

1. Field of the Invention

The invention relates to a cancer screening method, and in particular, to a cancer screening method using methylated DNA as the biomarker.

2. Description of the Prior Art

Cervical cancer has been one of the main causes of death in females worldwide and in Taiwan. Based on the statistical survey by the World Health Organization (WHO) in 2002, cervical cancer was the second major disease responsible for the death of women worldwide, second to breast cancer. Regular cervical cancer screening is the best way to prevent cervical cancer. Conventional cervical cancer screening includes two approaches: the most commonly used Pap smear, and human papilloma virus testing (HPV testing). Pap smear consists of sampling secreta from cervix uteri, examining under microscope whether there is cancerous pathological change in the exfoliated epithelial cell, so as to detect cervical cancer early. HPV testing, on the other hand, relies on the detection of human papilloma virus (HPV) DNA.

There are, however, many undesired properties of Pap smear. For one, it requires sampling by a physician, and analysis by a medical examiner/pathologist, which is a high cost of manpower that poses difficulty on promoting the test in many developing countries. Also, Pap smear has a high false negative rate which delays diagnosis and proper treatment prior to cancerous pathological change. As for HPV testing, although it is highly sensitive, it tends to create a high false positive rate, which not only leaves patients worry in vain, but also wastes much medical resources in examinations follow up to those false positive patients. Accordingly, one of the important topics in promoting cervical cancer examination relies on increasing the accuracy and convenience of cervical cancer examination method.

Infection with oncogenic human papilloma virus (HPV) is the most significant risk factor in the etiology of cervical cancer. E6/E7 oncoprotein encoded by "high-risk" HPV types has been shown to interact with the tumor-suppressor gene p53/pRB, causing abnormal cell-cycle regulation (zur Hausen 2000). HPV DNA could be detected in virtually all cases of cervical cancers (Walboomers, Jacobs et al. 1999). However, HPV infection is necessary but not sufficient to cause cervical cancer. About 60% of LSIL (low-grade squamous intraepithelial lesion) regress, 30% persists, 5-10% progress to high-grade SIL (HSIL, or High-grade squamous intraepithelial lesion) and only less than 1% becomes cervical cancer (Syrjanen, Vayrynen et al. 1985; Syrjanen 1996). Persistence of HPV infection and viral load may be detrimental accounting the development of HSIL and cancer (Ylitalo, Sorensen et al. 2000). However, the molecular mechanism of cervical carcinogenesis remains illusive.

Other factors, such as environmental and genetic alterations, may also play a decisive role in malignant conversion of cervical keratinocytes (Magnusson, Sparen et al. 1999; Ylitalo, Sorensen et al. 1999). Despite initiation by HPV, genetic changes with resultant genomic instability has long been recognized as an important mechanism for cervical carcinogenesis. Cytogenetic studies have revealed non-random chromosomal changes in cervical cancers (Mitra, Rao et al. 1994; Atkin and Baker 1997; Harris, Lu et al. 2003). Several molecular genetic studies have identified a few frequent loss of heterozygosity (LOH) sites, suggesting the involvement of tumor suppressor genes (TSGs) in the development of cervical cancer. (Mitra, Murty et al. 1994; Mullokandov, Kholodilov et al. 1996; Rader, Kamarasova et al. 1996; Kersemaekers, Hermans et al. 1998; Mitra 1999).

Genomic deletions have long been considered to be an important factor in tumorigenesis. For a long time, we have been accustomed to the idea that the coding potential of the genome lies within the arrangement of the four A, T, G, C bases. The two-hit theory proposed as early as in 1970s indicates concomitant mutations or deletions of some homologous tumor suppressor genes may cause or predispose to cancer development (Knudson, Hethcote et al. 1975; Knudson 2001). However, additional information that affects phenotype can be stored in the modified base 5-methylcytosine. 5-Methylcytosine is found in mammals in the context of the palindromic sequence 5'-CpG-3'. Most CpG dinucleotide pairs are methylated in mammalian cells except some areas called "CpG island." CpG islands are GC- and CpG-rich areas of approximately 1 kb, usually located in the vicinity of genes and often found near the promoter of widely expressed genes (Bird 1986; Larsen, Gundersen et al. 1992). Cytosine methylation occurs after DNA synthesis, by enzymatic transfer of a methyl group from the methyl donor S-adenosylmethionine to the carbon-5 position of cytosine. The enzymatic reaction is performed by DNA methyltransferases (DNMTs)(Laird 2003). DNMT1 is the main enzyme in mammals, and is responsible for the post-replicative restoration of hemi-methylated sites to full methylation, referred to as maintenance methylation, whereas DNMT3A and DNMT3B are thought to be involved primarily in methylating new sites, a process called de novo methylation (Okano, Bell et al. 1999; Robert, Morin et al. 2003).

Loss of methylation at CpG dinucleotides, i.e., general hypomethylation, was the first epigenetic abnormalities identified in cancer cells (Feinberg and Vogelstein 1983; Cheah, Wallace et al. 1984). However, during the past few years, it has become increasing apparent that site-specific hypermethylation, e.g., some tumor suppressor genes, is associated with loss of function which may provide selective advantages during carcinogenesis (Jones and Baylin 2002; Feinberg and Tycko 2004). Dense methylation of CpG islands at promoter regions can trigger chromatin remodeling through histone modifications with subsequent gene silencing (Geiman and Robertson 2002; Egger, Liang et al. 2004). Therefore, in addition to chromosomal deletions or genetic mutations, epigenetic silencing of tumor suppressor genes by promoter hypermethylation is commonly seen in human cancer (Baylin, Herman et al. 1998; Jones and Laird 1999; Baylin and Herman 2000).

Epidemiologic studies have recently shown the correlation of serum folate level, a major source of methyl group, with the infection and clearance of HPV (Piyathilake, Henao et al. 2004). Genetic polymorphisms of enzymes in the metabolism of methyl cycle were also reported to be associated with the development of cervical intraepithelial lesions (Henao, Piyathilake et al. 2004). As the concept of epigenetics evolves, studies exploring the association between DNA methylation and cervical cancer are also booming. Studies of DNA methylation in cervical cancer are accumulating, which showed the potential of using methylation as markers in cervical screening (Feng, Balasubramanian et al. 2005). With the nature of the interface between genetics and environment, the prevalence of methylation in tumor suppressor genes varies in different genes and different populations. The concept of methylator phenotypes with different disease behaviors was proposed with controversy. The methylator phenotype of cervical cancer and its interaction with HPV genotypes still remains unknown. The extent to which adenocarcinoma can be analogue to squamous cell carcinoma in terms of methylation patterns has never been investigated. What genes are specifically methylated in cervical cancer and how many genes are required to achieve clinical application will remain a blossoming issue in the coming future. The excavation of genes with higher contribution component to cervical carcinogenesis may shed light on the promise of using DNA methylation as a diagnostic marker as well as the development of a novel therapeutic intervention through epigenetic modulation.

SUMMARY OF THE INVENTION

The invention provides a cancer diagnostic method. The method uses the degree of methylation of a specific gene as the index to diagnose whether there is presence of cancer. The cancer diagnostic method according to the invention is applicable on the detection of cervical cancer. In addition to be the first line screening for cervical cancer, the cancer diagnostic method according to the invention can be used as the second line screening for cervical cancer in combination with or as an assistant to HPV testing in order to achieve a more accurate screening result for cervical cancer. Furthermore, the cancer diagnostic method according to the invention is capable of detecting other cancer types such as ovarian cancer, liver cancer and the like, to facilitate the diagnosis of other abnormal specimens.

In using the cancer diagnostic method according to the invention on the detection of cervical cancer, it exhibits a sensitivity and specificity higher than those of the Pap smear and HPV testing.

Accordingly, the invention provides a method for the diagnosis of cancer, characterized in that it comprises of detecting the methylation state of the target gene in the cell of the test specimen as a screening index to determine the existence of cancer, the method comprising the following steps:

step 1: providing a test specimen;
step 2: detecting the methylation state of the CpG sequence in at least one target gene within the genomic DNA of the test specimen, wherein the target genes is consisted of SOX1, PAX1, LMX1A, NKX6-1, WT1 and ONECUT1; and
step 3: determining whether there is cancer or cancerous pathological change in the specimen based on the presence or absence of the methylation state in the target gene.

The test specimens may be a cervical smear, ascites, blood, urine, feces, sputum, oral mucosa cell, gastric juice, bile, cervical epithelial cell and the like.

Method for detecting the methylation state of the CpG sequence in the target gene may be a methylation-specific PCR (MSP), quantitative methylation-specific PCR (QMSP), bisulfite sequencing (BS), microarrays, mass spectrometer, denaturing high-performance liquid chromatography (DH-PLC), and pyrosequencing.

The target gene SOX1 has a nucleotide sequence as depicted in SEQ ID No: 1.
The target gene PAX1 has a nucleotide sequence as depicted in SEQ ID No: 2.
The target gene LMX1A has a nucleotide sequence as depicted in SEQ ID No: 3.
The target gene NKX6-1 has a nucleotide sequence as depicted in SEQ ID No: 4.
The target gene WT1 has a nucleotide sequence as depicted in SEQ ID No: 5.
The target gene ONECUT1 has a nucleotide sequence as depicted in SEQ ID No: 6.

The invention provides a method for screening cervical cancer, characterized in that it comprises of detecting the methylation state of the target gene in the cell of the test specimen as a screening index to determine the existence of the cervical cancer, the method comprising the following steps:

step 1: providing a test specimen;
step 2: detecting the methylation state of the CpG sequence in at least one target gene within the genomic DNA of the test specimen, wherein the target genes is consisted of SOX1, PAX1, LMX1A, NKX6-1, WT1 and ONECUT1; and
step 3: determining whether there is cervical cancer or cancerous pathological change in the specimen based on the presence or absence of the methylation state in the target gene.

The test specimens may be a cervical smear, blood, urine, cervical epithelial cell and the like.

In one embodiment, the test specimen is a cervical smear.
In one embodiment, the test specimen is a cervical cell specimen exhibiting a positive HPV testing.

Method for detecting the methylation state of the CpG sequence in the target gene may be a methylation-specific PCR (MSP), quantitative methylation-specific PCR (QMSP), bisulfite sequencing (BS), microarrays, mass spectrometer, denaturing high-performance liquid chromatography (DH-PLC), and pyrosequencing.

The target gene SOX1 has a nucleotide sequence as depicted in SEQ ID No: 1.
The target gene PAX1 has a nucleotide sequence as depicted in SEQ ID No: 2.
The target gene LMX1A has a nucleotide sequence as depicted in SEQ ID No: 3.
The target gene NKX6-1 has a nucleotide sequence as depicted in SEQ ID No: 4.
The target gene WT1 has a nucleotide sequence as depicted in SEQ ID No: 5.
The target gene ONECUT1 has a nucleotide sequence as depicted in SEQ ID No: 6.

The invention provides further a method for screening ovarian cancer, characterized in that it comprises of detecting the methylation state of the target gene in the cell of the test specimen as a screening index to determine the existence of ovarian cancer, the method comprising following steps:

step 1: providing a test specimen;
step 2: detecting the methylation state of the CpG sequence in at least one target gene within the genomic DNA of the test specimen, wherein the target genes is consisted of SOX1, PAX1, and LMX1A; and
step 3: determining whether there is an ovarian cancer or cancerous pathological change in the specimen based on the presence or absence of the methylation state in the target gene.

The test specimens may be an ascites, blood, urine and the like.

Method for detecting the methylation state of the CpG sequence in the target gene may be a methylation-specific PCR (MSP), quantitative methylation-specific PCR (QMSP), bisulfite sequencing (BS), microarrays, mass spectrometer, denaturing high-performance liquid chromatography (DH-PLC), and pyrosequencing.

The target gene SOX1 has a nucleotide sequence as depicted in SEQ ID No: 1.
The target gene PAX1 has a nucleotide sequence as depicted in SEQ ID No: 2.
The target gene LMX1A has a nucleotide sequence as depicted in SEQ ID No: 3.

The invention provides further a method screening liver cancer, characterized in that it comprises of detecting the methylation state of the target gene in the cell of the test specimen as a screening index to determine the existence of liver cancer, the method comprising following steps:

step 1: providing a test specimen;

step 2: detecting the methylation state of the CpG sequence in at least one target gene within the genomic DNA of the test specimen, wherein the target genes is consisted of SOX1, and NKX6-1; and step 3: determining whether there is a liver cancer or cancerous pathological change in the specimen based on the presence or absence of the methylation state in the target gene.

The test specimens may be an ascites, blood, urine, feces, gastric juice, bile, and the like.

Method for detecting the methylation state of the CpG sequence in the target gene may be a methylation-specific PCR (MSP), quantitative methylation-specific PCR (QMSP), bisulfite sequencing (BS), microarrays, mass spectrometer, denaturing high-performance liquid chromatography (DHPLC), and pyrosequencing.

The target gene SOX1 has a nucleotide sequence as depicted in SEQ ID No: 1.

The target gene NKX6-1 has a nucleotide sequence as depicted in SEQ ID No: 4.

These features and advantages of the present invention will be fully understood and appreciated from the following detailed description of the accompanying Drawings.

DETAILED DESCRIPTION OF THE PREFERRED EMBODIMENT

EXAMPLE 1

Materials and Methods

1. Tissue Specimens

Figure 1:
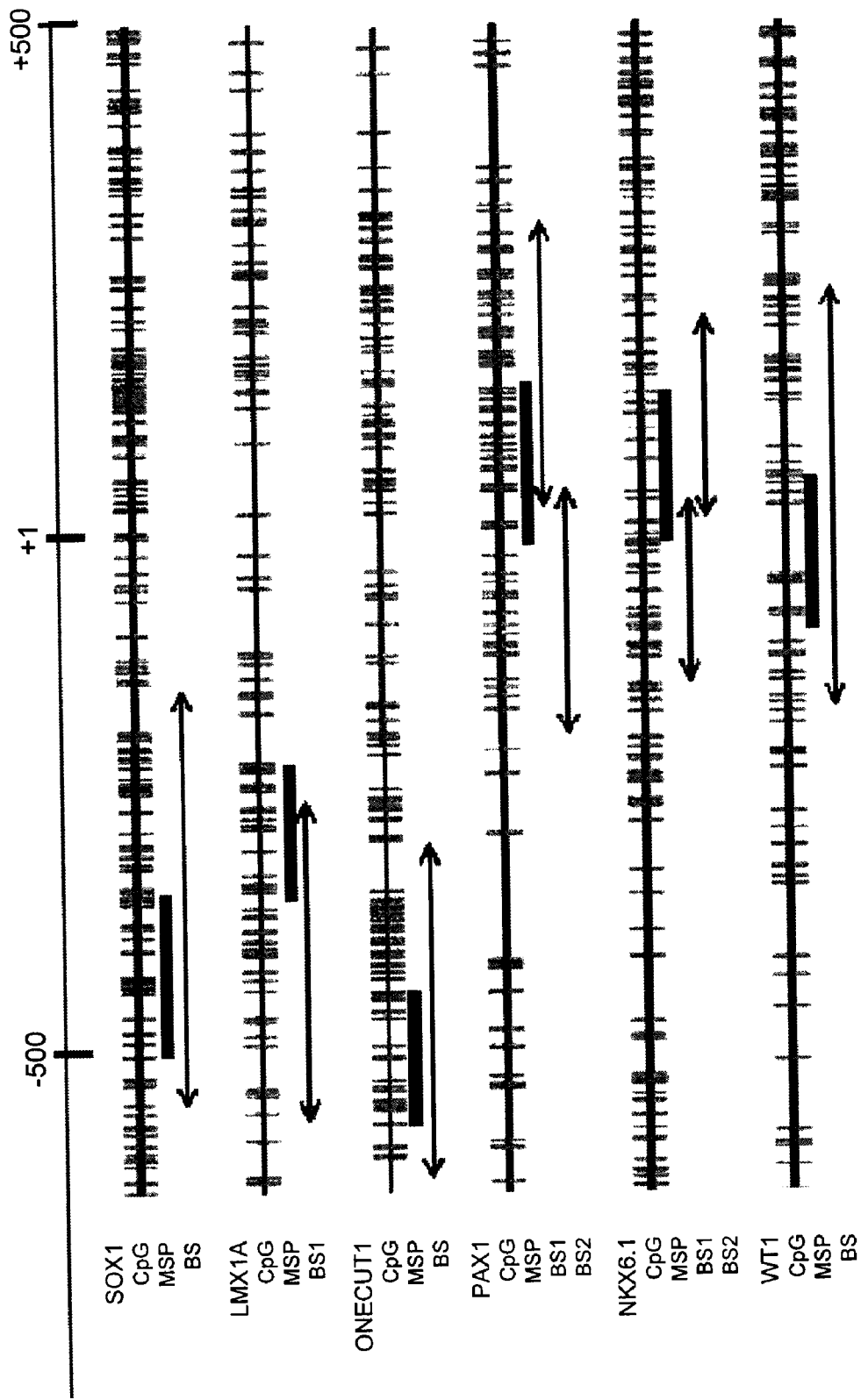
FIG. 1 shows the analysis of CpG sequences in various target gene used in the cancer screening method according to the invention, wherein CpG sequences in various genes are marked with ⌈ │⌋, positions occupied by synthetic fragments of MSP primers in various MSP genes are marked with ⌈→⌋, and positions occupied by synthetic fragments of bisulfite-sequenced primer in various genes are marked with ⌈↔⌋.

Cervical tissue specimens were obtained from patients with normal uterine cervixes (n=45) and patients with LSIL (n=45), HSIL (n=58), and invasive squamous cell carcinoma (SCC; n=109) of the uterine cervix. The patients were diagnosed, treated, and tissue banked at the Tri-Service General Hospital, Taipei, Taiwan, since 1993. For diagnostic purposes, cytological, histological, and clinical data for all patients were reviewed by a panel of colposcopists, cytologists, and pathologists. All patients were examined and treated using a standard hospital protocol for cervical neoplasia. Controls were recruited from healthy women who underwent routine Pap screening during the same period. Informed consent was obtained from all patients and control subjects. Exclusion criteria included pregnancy, chronic or acute viral infection, a history of cervical neoplasia, skin or genital warts, an immune-compromised state, the presence of other cancers, and past surgery of the uterine cervix. The study was approved by the Institutional Review Board of the Tri-Service General Hospital.

The tissue specimens also include a series of ovarian tumor samples, which were obtained from the tumor bank of Tri-Service General Hospital, and the ovarian samples include benign ovarian samples (n=36), borderline ovarian tumors (n=6), and malignancy ovarian tumors (n=122).

In addition, the liver samples used in the study includes normal liver samples (n=13), chronic hepatitis (n=15), cirrhosis of the liver (n=40), and hepatocellular carcinoma (HCC, n=54). All the liver samples were from the tumor bank of Tri-Service General Hospital.

2. Preparation of Genomic DNA

Genomic DNA was extracted from specimens using Qiagene DNA Extraction Kits. The concentration of DNA was determined using the PicoGreen fluorescence absorption method, and DNA quality was verified using agarose gel electrophoresis.

3. Differential Methylation Hybridization (DMH) Using CpG Island Microarrays

Differential Methylation Hybridization (DMH) was performed according to Yan et al. Pooled DNA from 30 cancer tissues and 10 normal cervical swabs were used for comparison. DNA was digested using MseI, ligated to linkers, and sequentially digested with methylation-sensitive restriction enzymes (HpaII and BstUI). The digested linker-ligated DNA was used as a template for polymerase chain reaction (PCR) amplification (20 cycles) and coupled to fluorescence dyes (Cy3: pooled normal cervical sample; Cy5: pooled cervical cancer sample) before hybridizing to the CpG island microarray containing 8,640 CpG island tags (University of Toronto). The identity of selected CpG islands (CGIs) was obtained from the CGI database (http://derlab.med.utoronto.ca/CpG-Islands/). The microarray data were analyzed using the circular-features mode of GenePix 6.0 software. Spots representing repetitive clones were flagged and unacceptable features were removed by filtering. Loci with ratios >2.0 were accepted as hypermethylated in the pooled cervical cancer sample.

4. Bisulfite Modification, Methylation-Specific PCR (MS-PCR), and Bisulfite Sequencing A DNA modification kit (Chemicon, Ternecula, Calif.) was used according to the manufacturer's recommendations to convert 1 μg aliquots of genomic DNA with sodium bisulfite to preserve the methylated cytosines. The final precipitate was eluted with 70 μl of prewarmed (55° C.) TE buffer for MS-PCR.

MS-PCR was performed according to Herman et al. (1996). In short, 1 μl of modified DNA was amplified using MS-PCR primers (table 1) that specifically recognized either the unmethylated or the methylated gene sequences present in the bisulfite-converted DNA. Methylation-specific PCR was done in a total volume of 25 μl containing 1 μl of modified template DNA, 1.5 pmol of each primer, 0.2 mmol/L deoxynucleotide triphosphates, and 1 unit of Gold Taq DNA polymerase (Applied Biosystems, Foster City, Calif.). MS-PCR reactions were subjected to an initial incubation at 95° C. for 5 min, followed by 35 cycles of 95° C. for 30 s, and annealing at the appropriate temperature for 30 s and at 72° C. for 30 s. The final extension was done at 72° C. for 5 min.

TABLE 1

The sequences of MS-PCR primers

| Gene | Primer | Sequence | |
|------|--------|----------|---|
| SOX1 | M Forward (F') | 5' CGTTTTTTTTTTTCGTTATTGGC 3' | (SEQ ID No: 7) |
|  | Reverse (R') | 5' CCTACGCTCGATCCTCAACG 3' | (SEQ ID No: 8) |
|  | U Forward (F') | 5' TGTTTTTTTTTTTTGTTATTGGTG 3' | (SEQ ID No: 9) |
|  | Reverse (R') | 5' CCTACACTCAATCCTCAACAAC 3' | (SEQ ID No: 10) |
| LMX1A | M Forward (F') | 5' TTTAGAAGCGGGCGGGAC 3' | (SEQ ID No: 11) |
|  | Reverse (R') | 5' CCGAATCCAAACACGCG 3' | (SEQ ID No: 12) |
|  | U Forward (F') | 5' GAGTTTAGAAGTGGGTGGGATG 3' | (SEQ ID No: 13) |
|  | Reverse (R') | 5' CAACCAAATCCAAACACACAAAAC 3' | (SEQ ID No: 14) |
| ONECUT1 | M Forward (F') | 5' TTGTAGCGGCGGTTTTAGGTC 3' | (SEQ ID No: 15) |
|  | Reverse (R') | 5' GCCAAACCCTTAACGTCCCG 3' | (SEQ ID No: 16) |
|  | U Forward (F') | 5' GATTGTAGTGGTGGTTTTAGGTTG 3' | (SEQ ID No: 17) |
|  | Reverse (R') | 5' CACCAAACCCTTAACATCCCAATAC 3' | (SEQ ID No: 18) |
| PAX1 | M Forward (F') | 5' TATTTTGGGTTTGGGGTCGC 3' | (SEQ ID No: 19) |
|  | Reverse (R') | 5' CCCGAAAACCGAAAACCG 3' | (SEQ ID No: 20) |
|  | U Forward (F') | 5' GTTTATTTTGGGTTTGGGGTTGTG 3' | (SEQ ID No: 21) |
|  | Reverse (R') | 5' CACCCAAAAACCAAAAACCAC 3' | (SEQ ID No: 22) |
| NKX6.1 | M Forward (F') | 5' CGTGGTCGTGGGATGTTAGC 3' | (SEQ ID No: 23) |
|  | Reverse (R') | 5' ACAAACAACGAAAAATACGCG 3' | (SEQ ID No: 24) |
|  | U Forward (F') | 5' GTGTGGTTGTGGGATGTTAGTG 3' | (SEQ ID No: 25) |
|  | Reverse (R') | 5' CAACAAACAACAAAAAATACACAAC 3' | (SEQ ID No: 26) |
| WT1 | M Forward (F') | 5' TGTTGAGTGAATGGAGCGGTC 3' | (SEQ ID No: 27) |
|  | Reverse (R') | 5' CGAAAAACCCCCGAATATAAACG 3' | (SEQ ID No: 28) |
|  | U Forward (F') | 5' GTTGTTGAGTGAATGGAGTGGTTG 3' | (SEQ ID No: 29) |
|  | Reverse (R') | 5' AATTACAAAAAACCCCCAAATATAAACAC 3' | (SEQ ID No: 30) |

M: The primers can specifically recognize the methylated gene sequences present in the bisulfite-converted DNA.
U: The primers can specifically recognize the unmethylated gene sequences present in the bisulfite-converted DNA.

Normal DNA from human peripheral blood was modified with sodium bisulfite and used as a control for the unmethylated promoter sequence. Normal human DNA was treated with SssI methyltransferase (New England Biolabs, Beverly, Mass.) to generate a positive control for methylated alleles. Amplification products were visualized on 2.5% agarose gel containing ethidium bromide and illuminated under UV light. All MS-PCR data were derived from at least two independent modifications of DNA. The absence of signal in duplicate experiments was scored as negative methylation. Bisulfite-treated genomic DNA was amplified using primers (table 2) and amplified PCR product was purified and cloned into pCR4-TOPO vectors (Invitrogen, Carlsbad, Calif.). Bisulfite sequencing was performed on at least five individual clones using the 377 automatic sequencer (Applied Biosystems, Foster City, Calif.).

TABLE 2

The sequences of Bisulfite sequencing primers

| Gene | Primer | | Sequence | |
|------|--------|---|----------|---|
| Sox1 | Forward (F') | 5' | GTTGTTTTYGGGTTTTTTTTGGTTG 3' | (SEQ ID No: 31) |
|      | Reverse (R') | 5' | ATTTCTCCTAATACACAAACCACTTACC 3' | (SEQ ID No: 32) |
| LMX1A | Forward (F') | 5' | TAGTTATTGGGAGAGAGTTYGTTTATTAG 3' | (SEQ ID No: 33) |
|       | Reverse (R') | 5' | CTACCCCAAATCRAAAAAAAACAC 3' | (SEQ ID No: 34) |
| ONECUT1 | Forward (F') | 5' | GAGTTTATTTAAGTAAGGGAGG 3' | (SEQ ID No: 35) |
|         | Reverse (R') | 5' | CAACTTAAACCATAACTCTATTACTATTAC 3' | (SEQ ID No: 36) |
| PAX1 | BS1 Forward (F') | 5' | GTGTTTTGGGAGGGGGTAGTAG 3' | (SEQ ID No: 37) |
|      | Reverse (R') | 5' | CCCTCCCRAACCCTACCTATC 3' | (SEQ ID No: 38) |
|      | BS2 Forward (F') | 5' | GATAGAAGGAGGGGGTAGAGTT 3' | (SEQ ID No: 39) |
|      | Reverse (R') | 5' | TACTACCCCCTCCCAAAACAC 3' | (SEQ ID No: 40) |
| NKX6.1 | BS1 Forward (F') | 5' | GGTATTTTTGGTTTAGTTGGTAGTT 3' | (SEQ ID No: 41) |
|        | Reverse (R') | 5' | AATACCCTCCATTACCCCCACC 3' | (SEQ ID No: 42) |
|        | BS2 Forward (F') | 5' | GGTGGGGGTAATGGAGGGTATT 3' | (SEQ ID No: 43) |
|        | Reverse (R') | 5' | CCTAAATTATAAATACCCAAAAAC 3' | (SEQ ID No: 44) |
| WT1 | Forward (F') | 5' | GTGTTGGGTTGAAGAGGAGGGTGT 3' | (SEQ ID No: 45) |
|     | Reverse (R') | 5' | ATCCTACAACAAAAAAAAATCCAAAATC 3' | (SEQ ID No: 46) |

5. Re-Expression of Methylated Genes by 5'-aza-2'-Deoxycytidine Treatment in Cancer Cell Lines The methylation status of candidate genes was tested in HeLa cervical cancer cell line using MS-PCR. Re-expression of methylated genes in cervical cancer cell lines after treatment with 10 μM of 5'-aza-2'-deoxycytidine (AZC) (Sigma Chemical Co.) for four days was assessed by RT-PCR. Total RNA was extracted using a Qiagen RNeasy kit (Qiagen, Valencia, Calif.). An additional DNase I digestion procedure (Qiagen) was included in the isolation of RNA to remove DNA contamination. One microgram of total RNA from each sample was subjected to cDNA synthesis using Superscript II reverse transcriptase and random hexamer (Invitrogen). The cDNA that was generated was used for PCR amplification with the reagents in the PCR master mix reagents kit (Applied Biosystems) as recommended by the manufacturer. The reactions were carried out in a thermal cycler (GeneAmp 2400 PE, Applied Biosystems). The primers and conditions for the PCR are listed in Table 3.

6. HPV Detection

The presence of HPV DNA in SCC was detected by L1 consensus PCR followed by a reverse line blot (Gravitt, et al., 1998; Lai, et al., 2005). DNA sequencing was used to verify novel HPV types that exceeded the detection spectrum of the hybridization procedure.

7. Statistical Analysis

Data analysis was carried out using statistical package SAS version 9.1. Associations between the methylation of genes and clinical parameters, including HPV status, were analyzed using a $X^2$ test and Fisher's exact test, wherever appropriate. Odds ratios (ORs) and 95% confidence intervals (95% CI) were calculated and adjusted for age and HPV infection using a logistic regression model. The alpha level of statistical significance was set at p=0.05. The sensitivity and specificity using HPV and methylation markers for the diagnosis of cervical lesions were calculated. The 95% CI was estimated using the BINOMIAL option in the EXACT statement.

TABLE 3

The sequences of MSP primers for RT-PCR

| Gene | Primer | | Sequence | |
|------|--------|---|----------|---|
| SOX1 | Forward (F') | 5' | AGACCTAGATGCCAACAATTGG 3' | (SEQ ID No: 47) |
|      | Reverse (R') | 5' | GCACCACTACGACTTAGTCCG 3' | (SEQ ID No: 48) |
| LMX1A | Forward (F') | 5' | GCTGCTTCTGCTGCTGTGTCT 3' | (SEQ ID No: 49) |
|       | Reverse (R') | 5' | ACGTTTGGGGCGCTTATGGTC 3' | (SEQ ID No: 50) |
| ONECUT1 | Forward (F') | 5' | CAAACCCTGGAGCAAACTCAA 3' | (SEQ ID No: 51) |
|         | Reverse (R') | 5' | TGTGTTGCCTCTATCCTTCCC 3' | (SEQ ID No: 52) |
| PAX1 | Forward (F') | 5' | CCTACGCTGCCCTACAACCACATC 3' | (SEQ ID No: 53) |
|      | Reverse (R') | 5' | TCACGCCGGCCCAGTCTTCCATCT 3' | (SEQ ID No: 54) |
| NKX6.1 | Forward (F') | 5' | CACACGAGACCCACTTTTTCC 3' | (SEQ ID No: 55) |
|        | Reverse (R') | 5' | CCCAACGAATAGGCCAAACG 3' | (SEQ ID No: 56) |
| WT1 | Forward (F') | 5' | GCTGTCCCACTTACAGATGCA 3' | (SEQ ID No: 57) |
|     | Reverse (R') | 5' | TCAAAGCGCCAGCTGGAGTTT 3' | (SEQ ID No: 58) |

EXAMPLE 2

Identification of Methylated Genes in Invasive Squamous Cell Carcinoma of the Cervix Differential methylation hybridization (DMH) was carried out by means of CpG island microarrays to screen out the highly methylated gene in cervical squamous cell carcinoma (SCC). The result from CpG island microarrays revealed that there were 216 points exhibited differential methylation between cervical cancer tissue specimens and normal cervical smears, of which, after taking off those having overlapped sequences, 26 gene promoter domain CpG islands (promoter CGIs).

Figure 2:
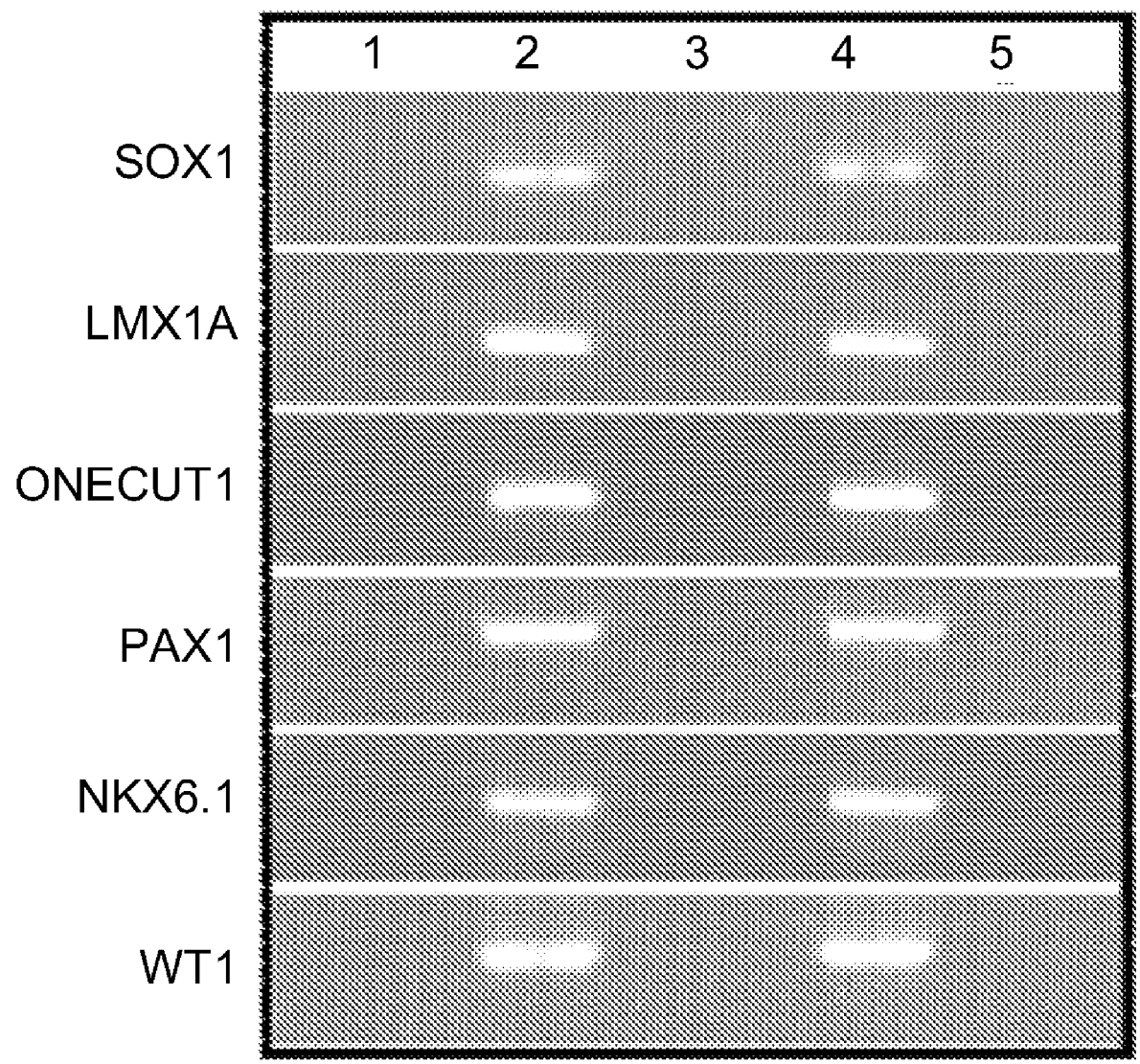
FIG. 2 shows results of methylation-specific PCR (MSP) analysis of various target genes used in the cancer screening method according to the invention, in mixed cervical cancer tissue specimens (a mixture of 30 specimens) as well as in mixed normal cervical smear specimens (a mixture of 10 specimens): the first column, mixed normal cervical smear specimens (a mixture of 10 specimens); the second column mixed cervical cancer tissue specimens (a mixture of 30 specimens); the third column, negative control; the fourth column, positive control; and the fifth column, blank control (water).
Figure 3:
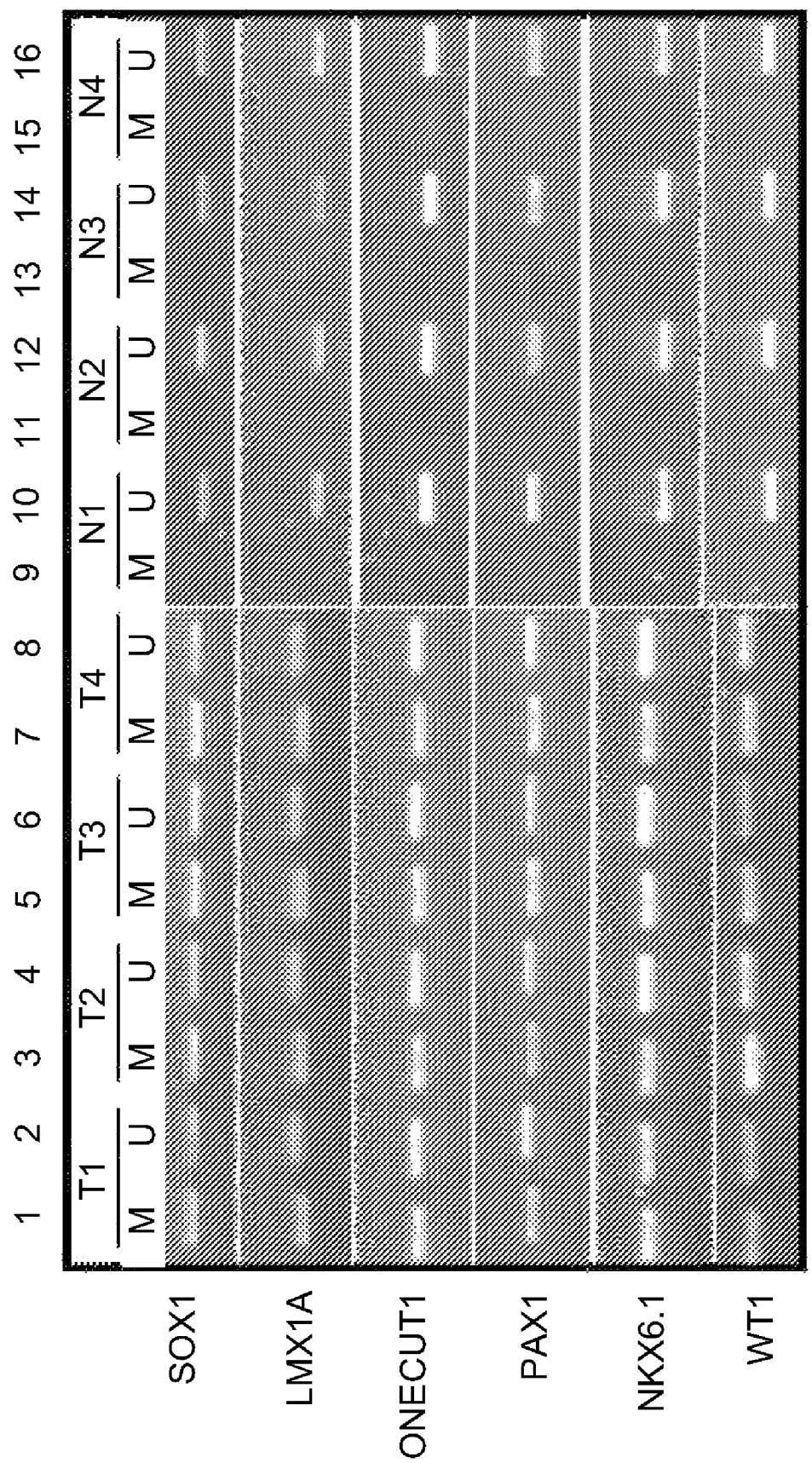
FIG. 3 shows results of methylation-specific PCR (MSP) analysis of various target genes used in the cancer screening method according to the invention, in individual cervical cancer tissue specimens as well as in individual normal cervical smear specimens: T1, T2, T3 and T4 represent 4 individual cervical cancer tissue specimens, while N1, N2, N3 and N4 represent 4 normal specimens; entries labeled with U indicate results from the methylation-specific PCR (MSP) conducted with MSP primers (U) that can recognize specifically the non-methylated gene sequences; while entries labeled with M indicate results from the methylation-specific PCR (MSP) conducted with MSP primers (M) that can recognize specifically the methylated gene sequences.

Sequencing and analysis were carried out on these gene promoter and 6 genes were selected. These genes included: SOX1 (SEQ ID No: 1), PAX1 (SEQ ID No: 2), LMX1A (SEQ ID No: 3), NKX6-1 (SEQ ID No: 4), WT1 (SEQ ID No: 5) and ONECUT1 (SEQ ID No: 6). Their detailed information were shown in Table 4. All of these 6 genes are important transcription factors in the development course, of which, SOX1, PAX1, LMX1A, NKX6-1, and WT1 were vital for the development of brain, roof plate, extremities, pancreatic island and urogenital organ, respectively, while ONECUT1 is important for the performance of hepatic and pancreatic genes. However, little correlation between these genes and cancer has been disclosed so far.

results shown in FIG. 2, these 6 genes exhibited methylation in mixed cervical cancer tissue specimens (as shown at column 2 in FIG. 2), while no methylation was occurred in mixed normal cervical smear specimens (as shown at column 1 in FIG. 2). Further testing was carried out with individual cervical cancer tissue specimen. Methylation-specific PCR (MSP) was performed on 4 cervical cancer tissue specimens (T1, T2, T3, T4) and 4 normal specimens (N1, N2, N3, N4), respectively, with MSP primer (U) that could recognize specifically non-methylated gene sequence as well as with MSP primer (M) that could recognize specifically methylated gene sequence. Results shown in FIG. 3 revealed that all of these 6 genes exhibited methylation in individual cervical cancer tissue specimen (as shown at columns 1, 3, 5, and 7 in FIG. 3), while no methylation could be detected in normal specimens with these same genes (as shown at columns 9, 11, 13, and 15 in FIG. 3). Based on the above-described results, these 6 genes were used as the methylation indicator genes for screening cervical cancer.

EXAMPLE 3

Association of DNA Methylation and Gene Expression in HeLa Cervical Cancer Cell Line In order to confirm whether the expression of cervical cancer methylation indicator gene is regulated through DNA

TABLE 4

Characteristics of methylated genes in cervical cancer that were identified using a CpG island microarray

| Gene | UniGene | Chromosomal location | Full name | Known molecular function |
|---|---|---|---|---|
| SOX1 | NM_005986 | 13q34 | Sex determining region Y-box 1 | DNA binding Transcription factor activity |
| PAX1 | NM_006192 | 20p11.2 | Paired box gene 1 | DNA binding |
| LMX1A | NM_177398 | 1q22-q23 | LIM homeobox transcription factor 1 alpha | Transcription factor activity Zinc ion binding |
| NKX6-1 | NM_006168 | 4q21.2-q22 | NK6 transcription factor related locus 1 | Transcription factor activity |
| ONECUT1 | NM_004498 | 15q21.1-q21.2 | One cut domain family member 1 | Transcription factor activity Transcriptional activator activity |
| WT1 | NM_024426 | 11p13 | Wilm's tumor 1 | Transcription factor activity Zinc ion binding |

CpG sequence analysis was carried out over about 500 bp nucleotides before and after each gene transcription initiation point (+1). As shown in FIG. 1, various genes containing CpG sequence are marked with ⌈ ⌋. MSP primer (as shown in Table 1) and bisulfite sequencing (BS) primer (as shown in Table 2) were designed with respect to each gene. Positions occupied by fragments synthesized during methylation-specific PCR (MSP) and bisulfite sequencing (BS) over various genes are shown also in FIG. 1.

Figure 4B:
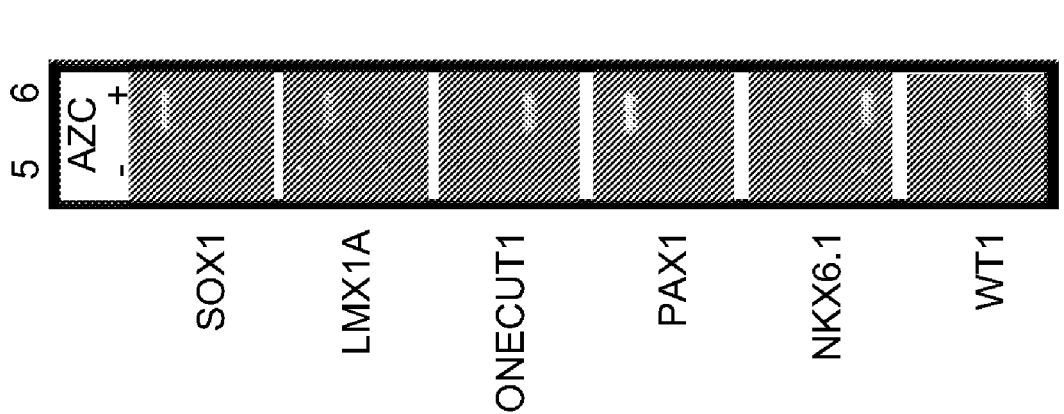
FIG. 4B shows results of RT-PCR analysis conducted with various target genes used in the cancer screening method according to the invention in non-5'-aza-2'-deoxycytidine-treated HeLacervical cancer cell line (AZC−, the fifth column), as well as in 5'-aza-2'-deoxycytidine-treated HeLacervical cancer cell line (AZC+, the sixth column).
Figure 4A:
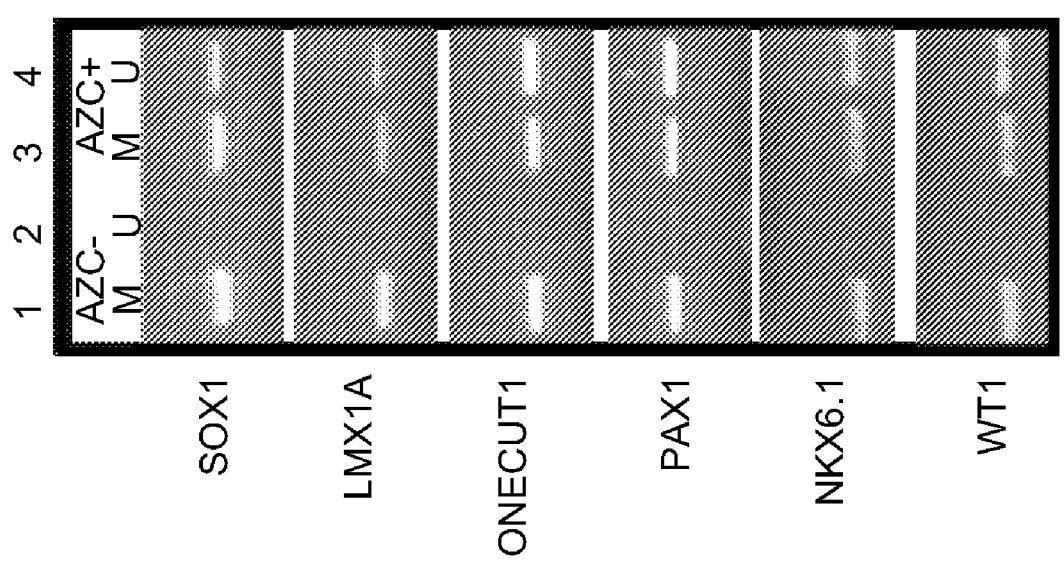
FIG. 4A shows results of methylation-specific PCR (MSP) analysis conducted with various target genes used in the cancer screening method according to the invention in non-5'-aza-2'-deoxycytidine-treated HeLacervical cancer cell line (AZC−, the first and second columns), as well as in 5'-aza-2'-deoxycytidine-treated HeLacervical cancer cell line (AZC+, the third and fourth columns); entries labeled with U indicate results from the methylation-specific PCR (MSP) conducted with MSP primers (U) that can recognize specifically the non-methylated gene sequences; while entries labeled with M indicate results from the methylation-specific PCR (MSP) conducted with MSP primers (M) that can recognize specifically the methylated gene sequences.

Then, methylation-specific PCR (MSP) analysis were carried out on mixed cervical cancer tissue specimens (a mixture of 30 specimens) as well as on mixed normal cervical smear specimens (a mixture of 10 specimens) in order to confirm whether the methylation phenomena of these 6 genes were different in different tissue specimens. As indicated from methylation, HeLa cervical cancer cell line was treated with 10 µM of DNA methyltransferase inhibitor, 5'-aza-2'-deoxycytidine (AZC) (Sigma Chemical Co.), for 4 days, following by checking the demethylation by the 6 gene promoters described above by means of methylation-specific PCR (MSP) carried out with MSP primer (U) that could recognize specifically non-methylated gene sequence, as well as with MSP primer (M) that could recognize specifically methylated gene sequence, respectively. Results as shown in FIG. 4A indicated that among non-5'-aza-2'-deoxycytidine (AZC)-treated HeLa cervical cancer cell lines (AZC−), 6 gene promoters exhibited methylated conditions (as shown at column 1 in FIG. 4A), and no non-methylated gene was detected (as shown at column 2 in FIG. 4A). On the other hand, after treated with 5'-aza-2'-deoxycytidine for 4 days, non-methylated target gene could be detected in HeLa cervical cancer cell lines (AZC+) (as shown at column 4 in FIG. 4A), indicating that through treated with methyltransferase inhibitor, 5'-aza-2'-deoxycytidine (AZC), the above-described 6 target genes had been demethylated partially.

Next, expressions of these 6 genes in HeLa cervical cancer cell line were analyzed through RT-PCR. Results shown in FIG. 4B indicated that in cell lines treated with 5'-aza-2'-deoxycytidine (AZC), mRNA of these 6 target genes could be detected (as shown at column 6 in FIG. 4B), while in those cell lines that had not been treated with 5'-aza-2'-deoxycytidine (AZC), no mRNA of any one target gene could be detected (as shown at column 5 in FIG. 4B). It is evident from these results that gene expression of these 6 target genes in cervical cancer cell could be modified actually through DNA methylation. As gene had been methylated, its expression could be inhibited, whereas after demethylated, the target gene could be re-expressed.

Figure 5:
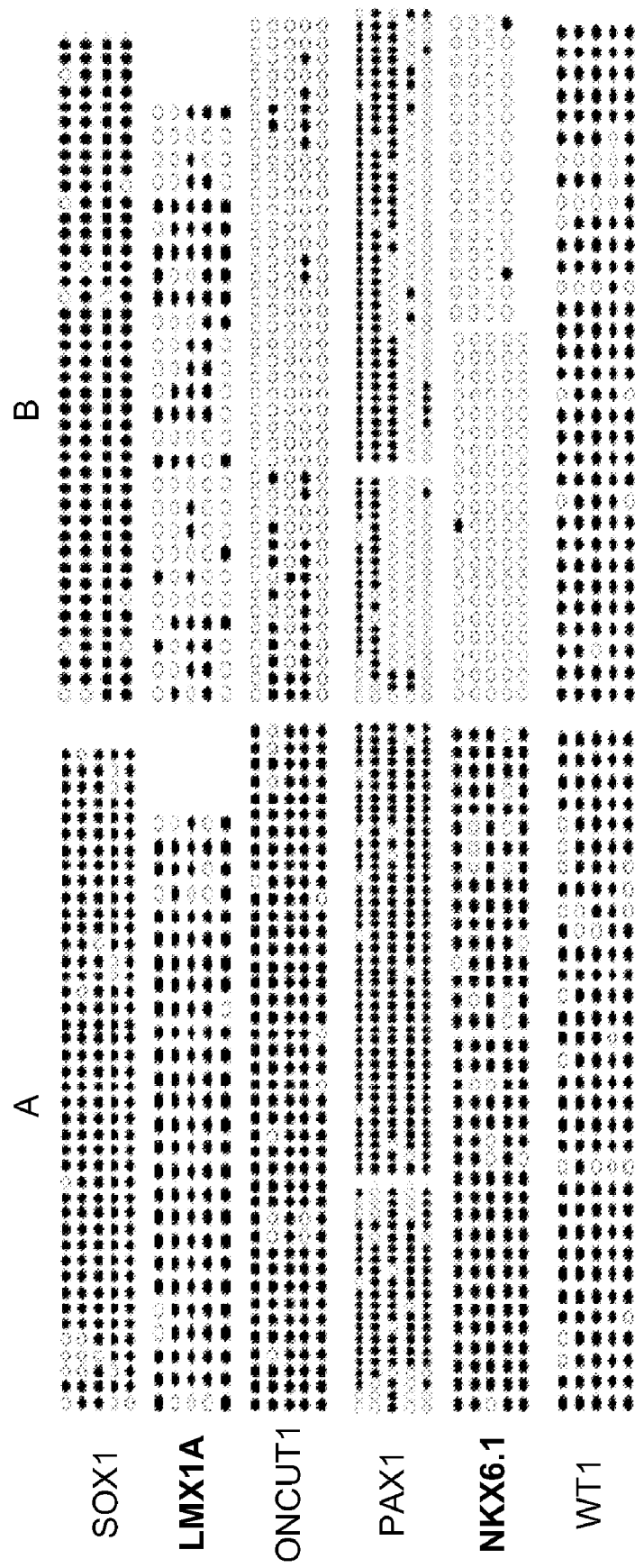
FIG. 5A shows results of bisulfite sequencing (BS) analysis conducted with various target genes used in the cancer screening method according to the invention in non-5'-aza-2'-deoxycytidine-treated HeLacervical cancer cell line.
FIG. 5B shows results of bisulfite sequencing (BS) analysis conducted with various target genes used in the cancer screening method according to the invention in 5'-aza-2'-deoxycytidine-treated HeLacervical cancer cell line.
Figure 6:
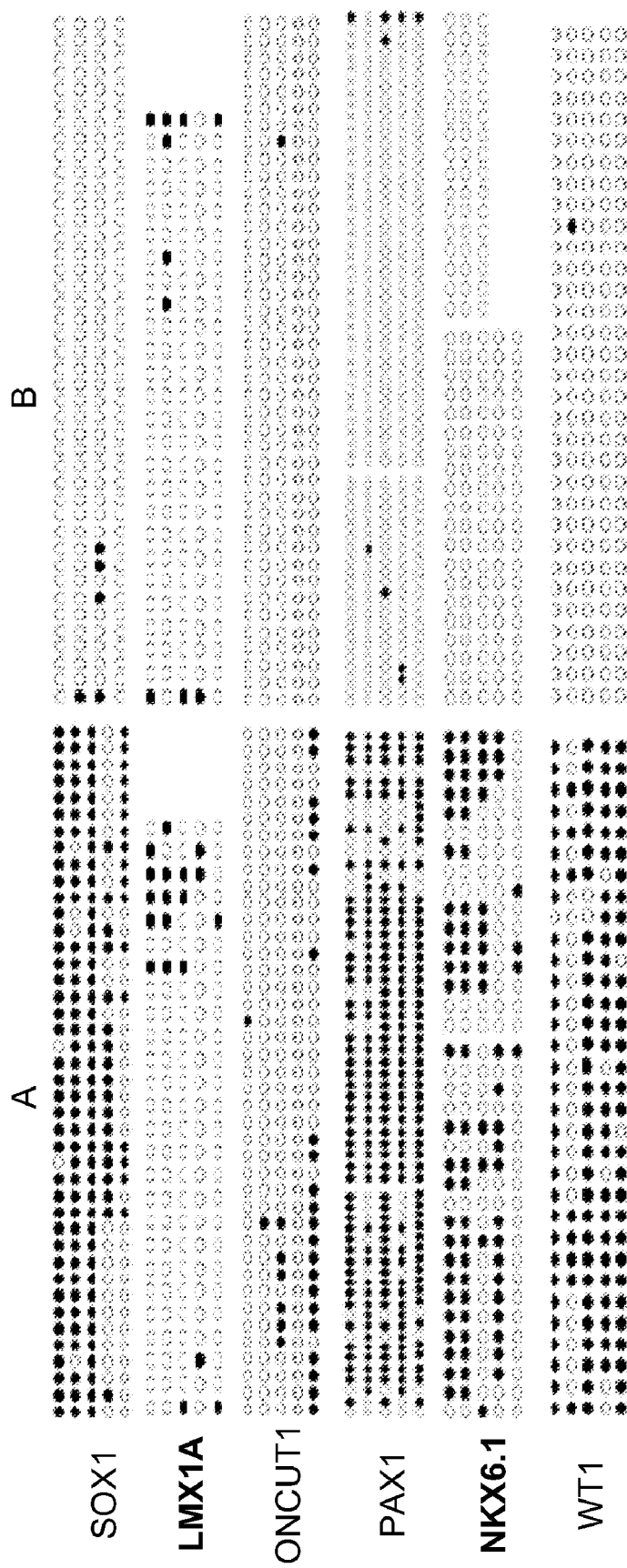
FIG. 6A shows results of bisulfite sequencing (BS) analysis conducted with various target genes used in the cancer screening method according to the invention in the cervical squamous cell carcinoma (SCC).
FIG. 6B shows results of bisulfite sequencing (BS) analysis conducted with various target genes used in the cancer screening method according to the invention in the normal specimen.

Furthermore, bisulfite sequencing (BS) was used to analyze whether the target gene in HeLa cervical cancer cell line exhibited hypermethylation condition. Results shown in FIG. 5 indicated that the number of hypermethylated target gene specimens in cell lines that had not been treated with 5'-aza-2'-deoxycytidine(AZC) (FIG. 5A) is higher than that in cell lines that had been treated with 5'-aza-2'-deoxycytidine (AZC) (FIG. 5B). Furthermore, cervical squamous cell carcinoma (SCC) and normal specimens were analyzed by means of bisulfite sequencing (BS) analysis. Results shown in FIG. 6 indicated that the number of hypermethylated target gene specimens in cervical squamous cell carcinoma (SCC) specimens (FIG. 6A) is considerably higher than that in normal specimens (FIG. 6B).

EXAMPLE 4

Methylation Analysis of Genes in Clinical Cervical Samples

The mean ages of patients with normal cervix and with LSIL, HSIL and SCC were 51.0±11.3, 39.7±9.6, 46.4±14.4 and 53.3±10.9 years, respectively (p<0.05). As shown in Table 5, the positive rate of high risk HPV DNA is 21.4%, 47.7%, 59.3% and 88.9% in normal, LSIL, HSIL and SCC, respectively (p<0.05). Patients with HPV infection showed significantly higher risk of the full spectrum of cervical lesions (OR: 3.1, 95% CI: 1.1-8.3; OR: 5.2, 95% CI: 2.1-13.0; OR: 29.9, 95% CI: 11.5-77.7 for LSIL, HSIL and SCC, respectively). All six genes (SOX1, PAX1, LMX1A, NKX6-1, WT1, and ONECUT1) showed frequent methylation in SCC (81.5%, 94.4%, 89.9%, 80.4%, 77.8%, and 20.4%, respectively), which was significantly greater than the methylation frequencies of their normal counterparts (2.2%, 0%, 6.7%, 11.9%, 11.1% and 0%, respectively; p≦0.001).

The methylation frequency of NKX6-1 was 53.3% in LSIL, 55.1% in HSIL, and 80.4% in SCC. Patients with methylations of NKX6-1 showed higher risks of SCC (OR: 29.8, 95% CI: 10.4-85.2). The methylation frequency of PAX1 was 2.3% in LSIL, 42.1% in HSIL, and 94.4% in SCC. Patients with methylations of PAX1 showed higher risks of HSIL and SCC (OR: >999.9, 95% CI:<0.1→999.9; OR:>999.9, 95% CI:<0.1→999.9, respectively).

The methylation rates of SOX1, LMX1A, and ONECUT1 were low in precancerous lesions, but increased substantially between HSIL and SCC (9.3% vs. 81.5%, 16% vs. 89.9%, and 7.4% vs. 20.4%, respectively). Patients with methylations of SOX1, LMX1A and ONECUT1 showed higher risks of SCC (OR: 200.2, 95% CI: 25.8-999.9; OR: 124.5, 95% CI: 33.0-470.1; OR: 7.3, 95% CI: 2.0-25.9, respectively). WT1 exhibited a severity-dependent increase in methylation frequency (11.1% in normal, 20.0% in LSIL, 42.1% in HSIL, and 77.8% in SCC). Patients with methylations of WT1 showed higher risks of HSIL and SCC (OR: 6.7, 95% CI: 2.2-19.8; OR: 27.9, 95% CI: 9.8-78.9, respectively).

EXAMPLE 5

Diagnostic Performance of DNA Methylation Markers

The sensitivities and specificities of HPV and DNA methylations were determined to assess their usefulness as biomarkers for diagnosis of high-grade cervical lesions and invasive cervical cancer. As shown in Table 6, the sensitivity and specificity for the diagnosis of SCC using HPV testing were 83.1% and 85.5%, respectively (95% CI: 77.6-88.5 and 79.6-91.4, respectively). SOX1, PAX1, LMX1A, NKX6-1, and WT1 methylations had high sensitivities (77.8%-94.4%) and specificities (88.1%-100%) for diagnosis of SCC.

When combined parallel testing (CPT) was applied for HPV and each methylation marker, which means that either one being positive was counted as positive, the sensitivities and specificities were in the ranges of 97.2%-98.2% and 66.7%-79.5%, respectively. When combined sequential testing (CST) was applied for HPV and each methylation marker, which means testing for HPV first with methylation detection following for HPV (+) patients, the sensitivities were in the ranges of 69.4%-85.0%. All the specificities were 100%.

When HSIL and SCC were present, the sensitivity and specificity for the diagnosis of HSIL/SCC using HPV testing were 75.0% (95% CI 70.2-79.8) and 85.5% (95% CI 79.6-91.4), respectively. The sensitivities and specificities of SOX1, PAX1, LMX1A, NKX6-1 and WT1 methylations were in the ranges of 57.4%-76.2% and 88.1%-100%, respectively. Using CPT for HPV and each methylation marker, the sensitivities could be improved to 85.8%-94.9%. Using CST for HPV and each methylation marker, all the specificities were 100%. When CPT was done using HPV and the methylations of SOX1, PAX1 and LMX1A, the sensitivities could be 100% for SCC and 93.4% for HSIL/SCC. PAX1 conferred the best performance when used alone with sensitivities of 94.4% (95% CI 90.0-98.8) and 76.2% (95% CI 69.7-82.7) for SCC and HSIL/SCC, respectively. The specificities were both 100%.

TABLE 5

Clinical relevance of DNA methylations in the full spectrum of cervical neoplasias

| Clinical status/ genes | SOX1 | PAX1 | LMX1A | NKX6-1 | WT1 | ONECUT1 | HPV |
|---|---|---|---|---|---|---|---|
| Normal (n = 45) | 1/45 (2.2%) | 0/41 (0%) | 3/45 (6.7%) | 5/42 (11.9%) | 5/45 (11.1%) | 0/45 (0%) | 9/42 (21.4%) |

TABLE 5-continued

Clinical relevance of DNA methylations in the full spectrum of cervical neoplasias

| Clinical status/ genes | SOX1 | PAX1 | LMX1A | NKX6-1 | WT1 | ONECUT1 | HPV |
|---|---|---|---|---|---|---|---|
| LSIL | 2/45 | 1/44 | 6/45 | 24/45 | 9/45 | 3/45 | 21/44 |
| (n = 45) | (4.4%) | (2.3%) | (13.3%) | (53.3%) | (20.0%) | (6.7%) | (47.7%) |
| OR | 2.0 | — | 2.2 | 8.5 | 2.0 | — | 3.3 |
| (95% CI) | (0.2-23.4) | — | (0.5-9.2) | (2.8-25.5) | (0.6-6.5) | — | (1.3-8.6) |
| OR* | 3.1 | — | 2.2 | 9.6 | 2.7 | — | 3.1 |
| (95% CI) | (0.3-36.7) | — | (0.5-9.7) | (3.1-30.4) | (0.8-9.3) | — | (1.1-8.3) |
| HSIL | 5/54 | 24/57 | 8/50 | 27/49 | 24/57 | 4/54 | 32/54 |
| (n = 58) | (9.3%) | (42.1%) | (16.0%) | (55.1%) | (42.1%) | (7.4%) | (59.3%) |
| OR | 4.5 | >999.9 | 2.7 | 9.1 | 5.8 | 2.3 | 5.3 |
| (95% CI) | (0.5-39.9) | (<0.1->999.9) | (0.6-10.7) | (3.1-27.0) | (2.0-16.9) | (0.5-10.8) | (2.1-13.3) |
| OR* | 5.1 | >999.9 | 2.7 | 9.6 | 6.7 | 2.3 | 5.2 |
| (95% CI) | (0.6-45.9) | (<0.1->999.9) | (0.7-10.9) | (3.2-29.1) | (2.2-19.8) | (0.5-10.8) | (2.1-13.0) |
| SCC | 88/108 | 101/107 | 98/109 | 86/107 | 84/108 | 22/108 | 96/108 |
| (n = 109) | (81.5%) | (94.4%) | (89.9%) | (80.4%) | (77.8%) | (20.4%) | (88.9%) |
| OR | 193.5 | >999.9 | 124.7 | 30.3 | 28.0 | 7.4 | 29.3 |
| (95% CI) | (25.2-1000) | (<0.1->999.9) | (33.1-469.9) | (10.6-86.5) | (10.0-78.8) | (2.1-25.7) | (11.3-75.8) |
| OR* | 200.2 | >999.9 | 124.5 | 29.8 | 27.9 | 7.3 | 29.9 |
| (95% CI) | (25.8-999.9) | (<0.1->999.9) | (33.0-470.1) | (10.4-85.2) | (9.8-78.9) | (2.0-25.9) | (11.5-77.7) |
| Probability | p < 0.0001 | p < 0.0001 | p < 0.0001 | p < 0.0001 | p < 0.0001 | p = 0.001 | p < 0.0001 |

*adjusted for age and HPV infection

TABLE 6

The sensitivities and specificities of HPV testing and DNA methylations for high-grade cervical lesions and invasive cervical cancer.

| Biomarker | Test | SCC OR | Sensitivity (95% CI) | OR | Specificity (95% CI) | HSIL/SCC OR | Sensitivity (95% CI) | OR | Specificity (95% CI) |
|---|---|---|---|---|---|---|---|---|---|
| HPV | alone | 83.1 | (77.6-88.5) | 85.5 | (79.6-91.4) | 75.0 | (70.2-79.8) | 85.5 | (79.6-91.4) |
| SOX1 | alone | 81.5 | (74.2-88.8) | 97.6 | (93.0-100.0) | 57.4 | (49.8-65.0) | 97.6 | (93.0-100.0) |
|  | CPT | 98.1 | (95.6-100.0) | 76.2 | (63.3-89.1) | 85.8 | (80.4-91.2) | 76.2 | (63.3-89.1) |
|  | CST | 72.2 | (63.8-80.7) | 100.0 | (100.0-100.0) | 50.6 | (42.9-58.3) | 100.0 | (100.0-100.0) |
| PAX1 | alone | 94.4 | (90.0-98.8) | 100.0 | (100.0-100.0) | 76.2 | (69.7-82.7) | 100.0 | (100.0-100.0) |
|  | CPT | 98.1 | (95.6-100.0) | 79.5 | (66.8-92.2) | 89.6 | (85.0-94.3) | 79.5 | (66.8-92.2) |
|  | CST | 85.0 | (78.3-91.8) | 100.0 | (100.0-100.0) | 65.2 | (58.0-72.5) | 100.0 | (100.0-100.0) |
| LMX1A | alone | 89.9 | (84.3-95.6) | 92.9 | (85.1-100.0) | 66.7 | (59.3-74.0) | 92.9 | (85.1-100.0) |
|  | CPT | 98.2 | (95.7-100.0) | 71.4 | (57.8-85.1) | 89.3 | (84.5-94.1) | 71.4 | (57.8-85.1) |
|  | CST | 80.7 | (73.3-88.1) | 100.0 | (100.0-100.0) | 58.5 | (50.8-66.2) | 100.0 | (100.0-100.0) |
| NKX6-1 | alone | 80.4 | (72.9-87.9) | 90.0 | (80.7-99.3) | 72.4 | (65.4-79.5) | 90.0 | (80.7-99.3) |
|  | CPT | 98.1 | (95.6-100.0) | 70.0 | (55.8-84.2) | 94.9 | (91.4-98.3) | 70.0 | (55.8-84.2) |
|  | CST | 71.0 | (62.4-79.6) | 100.0 | (100.0-100.0) | 59.0 | (51.3-66.7) | 100.0 | (100.0-100.0) |
| WT1 | alone | 77.8 | (69.9-85.6) | 88.1 | (78.3-97.9) | 65.5 | (58.2-72.7) | 88.1 | (78.3-97.9) |
|  | CPT | 97.2 | (94.1-100.0) | 66.7 | (52.4-80.9) | 90.3 | (85.8-94.8) | 66.7 | (52.4-80.9) |
|  | CST | 69.4 | (60.8-78.1) | 100.0 | (100.0-100.0) | 53.9 | (46.3-61.5) | 100.0 | (100.0-100.0) |
| HPV +SOX1 +PAX1 +LMX1A | CPT | 100.0 | (100.0-100.0) | 69.2 | (54.8-83.7) | 93.4 | (89.4-97.3) | 69.2 | (54.8-83.7) |

EXAMPLE 6

Methylation Analysis of Genes in Ovarian Samples

MS-PCR was performed to analyze the methylation status of the target genes in ovarian samples. As shown in Table 7, the promoters of SOX1, PAX1, and LMX1A were methylated neither in benign ovarian samples nor in borderline ovarian tumors. However, the methylation frequency of these 3 genes, SOX1, PAX1, and LMX1A, was significantly greater in malignancy ovarian tumors. The methylation frequency of SOX1, PAX1, and LMX1A was 55.7%, 49.2%, and 32.8%, respectively.

TABLE 7

Clinical relevance of DNA methylations in ovarian samples

| Clinical status/genes | SOX1 | PAX1 | LMX1A |
|---|---|---|---|
| Benign (n = 36) | 0/36 (0.0) | 0/36 (0.0) | 0/36 (0.0) |
| Borderline (n = 6) | 0/6 (0.0) | 0/36 (0.0) | 0/36 (0.0) |
| Malignancy (n = 122) | 68/54 (55.7) | 60/122 (49.2) | 40/122 (32.8) |
| Probability | p < 0.0001 | p < 0.0001 | p < 0.0001 |

EXAMPLE 7

Methylation Analysis of Genes in Liver Samples

MS-PCR was performed to analyze the methylation status of the target genes in liver samples. As shown in Table 8, the methylation frequency of SOX1 was significantly greater in abnormal liver samples than in normal liver samples, and the frequency was 7.7%, 33.3%, 27.5%, and 53.7% in normal liver samples, chronic hepatitis, cirrhosis of the liver, and hepatocellular carcinoma (HCC) respectively. Moreover, the methylation frequency of NKX6-1 was significantly greater in hepatocellular carcinoma (HCC) (57%) than in normal liver samples (10%).

TABLE 8

Clinical relevance of DNA methylations in liver samples

| Clinical status/genes | SOX1 | NKX6-1 |
|---|---|---|
| Normal liver (n = 13) | 1/13 (7.7) | 1/10 (10) |
| Chronic Hepatitis (n = 15) | 5/15 (33.3) | — |
| Cirrhosis (n = 40) | 11/40 (27.5) | — |
| HCC (n = 54) | 29/54 (53.7) | 12/21 (57) |
| Probability | P = 0.005 | P < 0.05 |

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A method of screening for cervical cancer in a human patient comprising:
   (i) obtaining a biological sample comprising cervical cells from the patient,
   (ii) determining a degree of methylation of a CpG sequence of SOX1, PAX1, LMX1A, NKX6-1, WT1 and ONE-CUT1 in the sample, and
   (iii) comparing a level of methylation of the CpG sequence of SOX1, PAX1, LMX1A, NKX6-1, WT1 and ONE-CUT1 in the sample with the level of methylation in normal cervical cells; wherein a higher degree of methylation in the sample compared to normal cervical cells indicates an increased likelihood of cervical cancer.

2. A method of screening for cervical cancer as recited in claim 1, wherein a target gene SOX1 has a nucleotide sequence as depicted in SEQ ID No: 1.

3. A method of screening for cervical cancer as recited in claim 1, wherein a target gene PAX1 has a nucleotide sequence as depicted in SEQ ID No: 2.

4. A method of screening for cervical cancer as recited in claim 1, wherein a target gene LMX1A has a nucleotide sequence as depicted in SEQ ID No: 3.

5. A method of screening for cervical cancer as recited in claim 1, wherein a target gene NKX6-1 has a nucleotide sequence as depicted in SEQ ID No: 4.

6. A method of screening for cervical cancer as recited in claim 1, wherein a target gene WT1 has a nucleotide sequence as depicted in SEQ ID No: 5.

7. A method of screening for cervical cancer as recited in claim 1, wherein a target gene ONECUT1 has a nucleotide sequence as depicted in SEQ ID No: 6.

* * * * *